(12) United States Patent
Fosdick et al.

(10) Patent No.: US 7,816,514 B2
(45) Date of Patent: *Oct. 19, 2010

(54) GLUCOSAMINE AND METHOD OF MAKING GLUCOSAMINE FROM MICROBIAL BIOMASS

(75) Inventors: Lawrence E. Fosdick, Oskaloosa, IA (US); John A. Bohlmann, Ottumwa, IA (US); James R. Trinkle, Bussey, IA (US); Brenda L. Ray, Ottumwa, IA (US)

(73) Assignee: Cargill, Incorporated, Wayzata, MN (US)

( * ) Notice: Subject to any disclaimer, the term of this patent is extended or adjusted under 35 U.S.C. 154(b) by 688 days.

This patent is subject to a terminal disclaimer.

(21) Appl. No.: 10/685,125

(22) Filed: Oct. 13, 2003

(65) Prior Publication Data

US 2004/0077055 A1    Apr. 22, 2004

Related U.S. Application Data

(63) Continuation-in-part of application No. 10/326,549, filed on Dec. 19, 2002, now Pat. No. 7,049,433, which is a continuation of application No. 09/785,695, filed on Feb. 16, 2001, now abandoned.

(51) Int. Cl.
*C07H 5/04* (2006.01)
*C07H 5/06* (2006.01)

(52) U.S. Cl. .................. 536/55.3; 536/55.2

(58) Field of Classification Search .............. 514/62; 536/55.2, 55.3
See application file for complete search history.

(56) References Cited

U.S. PATENT DOCUMENTS

| | | |
|---|---|---|
| 2,040,879 A | 5/1936 | Rigby |
| 3,232,836 A | 2/1966 | Carlozzi et al. |
| 3,632,754 A | 1/1972 | Balassa |
| 3,683,076 A | 8/1972 | Robati |
| 3,903,268 A | 9/1975 | Balassa |
| 3,911,116 A | 10/1975 | Balassa |
| 3,914,413 A | 10/1975 | Balassa |
| 4,034,121 A | 7/1977 | Dunn et al. |
| 4,056,432 A | 11/1977 | Slagel et al. |
| 4,211,846 A | 7/1980 | Lafferty |
| 4,282,351 A | 8/1981 | Muzzarelli |
| 4,642,340 A | 2/1987 | Senin et al. |
| 4,806,474 A | 2/1989 | Hershberger |
| 4,886,541 A | 12/1989 | Hadwiger |
| 4,948,881 A | 8/1990 | Naggi et al. |
| 4,954,440 A | 9/1990 | Johal et al. |
| 4,970,150 A | 11/1990 | Yaku et al. |
| 4,983,304 A | 1/1991 | Tsugita et al. |
| 5,141,964 A | 8/1992 | Noel |
| 5,219,749 A | 6/1993 | Bouriotis et al. |
| 5,232,842 A | 8/1993 | Park et al. |
| 5,262,310 A | 11/1993 | Karube et al. |
| 5,702,939 A | 12/1997 | Fujishima et al. |
| 5,730,876 A | 3/1998 | You et al. |
| 5,843,923 A | 12/1998 | Schleck et al. |
| 5,859,263 A | 1/1999 | Ghorpade et al. |
| 5,902,801 A | 5/1999 | Schleck et al. |
| 5,905,035 A | 5/1999 | Okada et al. |
| 5,985,644 A | 11/1999 | Roseman et al. |
| 5,998,173 A | 12/1999 | Haynes et al. |
| 6,117,851 A | 9/2000 | Sherman et al. |
| 6,225,493 B1 | 5/2001 | Prakash et al. |
| 6,248,570 B1 | 6/2001 | Michon et al. |
| 6,333,399 B1 | 12/2001 | Teslenko et al. |
| 6,372,457 B1 * | 4/2002 | Berry et al. .................. 435/72 |
| 6,432,929 B1 | 8/2002 | Stone |
| 6,486,307 B1 | 11/2002 | Gandhi et al. |
| 6,693,188 B2 | 2/2004 | Bohlmann et al. |
| H2218 H | 6/2005 | Hwang et al. |
| 2002/0160459 A1 | 10/2002 | Berry et al. |
| 2003/0134825 A1 | 7/2003 | Bahoshy |
| 2003/0138543 A1 | 7/2003 | Bahoshy |
| 2003/0170374 A1 | 9/2003 | Bahoshy |
| 2003/0181419 A1 | 9/2003 | Hwang et al. |
| 2005/0130273 A1 | 6/2005 | Versali et al. |
| 2006/0172392 A1 | 8/2006 | Zhou et al. |
| 2006/0178344 A1 | 8/2006 | Anderson et al. |

FOREIGN PATENT DOCUMENTS

| | | |
|---|---|---|
| CS | 209258 | 5/1983 |
| EP | 566 349 | 10/1993 |
| EP | 768 320 | 4/1997 |
| EP | 0 885 954 A1 | 12/1998 |
| EP | 997 480 | 5/2000 |
| GB | 458839 | 12/1936 |
| GB | 785525 | 10/1957 |

(Continued)

OTHER PUBLICATIONS

Database Caplus on STN: Accession No. 1976-519336 (1976).
Database Caplus on STN: Accession No. 1999:816485 (1999).
Domanski et al., "Use of a Chitinase Complex and β-(1,3)-Glucanase for Spheroplast Production from *Candida albicans*," J. Bacteriol. 96:270-271 (1968).
Eichner, "Antioxidative Effect of Maillard Reaction Intermediates," Prog. Fd. Nutr. Sci., 5:441-451 (1981).
Ghorpade et al., "Industrial Applications for Levulinic Acid," Industrial Agricultural Product Center, University of Nebraska (visited Oct. 8, 2003) <http://agproducts.unl.edu/levu.htm> 8 pp.

(Continued)

*Primary Examiner*—Elli Peselev
(74) *Attorney, Agent, or Firm*—Klarquist Sparkman, LLP

(57) ABSTRACT

Glucosamine suitable for human or animal consumption is disclosed. The glucosamine is derived from fungal biomass containing chitin. Various methods of producing glucosamine by acid hydrolysis of fermented fungal biomass are also disclosed.

22 Claims, 8 Drawing Sheets

FOREIGN PATENT DOCUMENTS

| | | |
|---|---|---|
| GB | 833264 | 4/1960 |
| GB | 896940 | 5/1962 |
| JP | 53-18794 | 2/1978 |
| JP | 55012109 | 1/1980 |
| JP | 62070401 A2 | 3/1987 |
| JP | 63097633 A2 | 4/1988 |
| JP | 63225602 A2 | 9/1988 |
| JP | 2149335 A2 | 6/1990 |
| JP | 2180903 A2 | 7/1990 |
| JP | 2200196 A2 | 8/1990 |
| JP | 2229832 A2 | 9/1990 |
| JP | 2258740 A2 | 10/1990 |
| JP | 5068580 A2 | 10/1993 |
| JP | 7330808 A2 | 12/1995 |
| JP | 8-41106 A | 2/1996 |
| JP | 10297913 A2 | 11/1998 |
| JP | 2000281696 | 10/2000 |
| JP | 2001-292792 | 10/2001 |
| WO | WO 98/30713 | 7/1998 |
| WO | WO 98/42755 | 10/1998 |
| WO | 99 41294 | 8/1999 |
| WO | WO 00/04182 | 1/2000 |
| WO | WO 0101992 A1 | 1/2001 |
| WO | WO 01/93847 A2 | 12/2001 |
| WO | WO 01/93847 A3 | 12/2001 |
| WO | WO 03/013435 A2 | 2/2003 |

OTHER PUBLICATIONS

Gomyo et al., "On the Interaction of Melanoidin with Metallic Ions," Agr. Biol. Chem., 40(1):33-40 (1976).

Hayase et al., "Scavenging of Active Oxygens by Melanoidins," Agric. Biol. Chem., 53(12):3383-3385 (1989).

Huang et al., "Development and Validation of Oxygen Radical Absorbance Capacity Assay for Lipophilic Antioxidants Using Randomly Methylated β-Cyclodextrin as the Solubility Enhancer," J. Agric. Food Chem., 7 pp. (2002).

Huang et al., "High-Throughput Assay of Oxygen Radical Absorbance Capacity (ORAC) Using a Multichannel Liquid Handling System Coupled with a Microplate Fluorescence Reader in 96-Well Format," J. Agric. Food Chem., 50:4437-4444 (2002).

Ou et al., "Analysis of Antioxidant Activities of Common Vegetables Employing Oxygen Radical Absorbance Capacity (ORAC) and Ferric Reducing Antioxidant Power (FRAP) Assays: A Comparative Study," J. Agric. Food Chem., 7 pp. (2002).

Xin et al., "Primary study on the production of chitosan by the method of culturing microorganism," Food Science, p. 22 (3 pp.), Jul. 1997 (and a partial English translation).

Yen et al., "Antioxidant and Prooxidant activity of Xylose-Lysine Maillard Reaction Products," The Maillard Reaction in Foods and Medicine, Ed. J. O'Brien et al., pp. 231-236 (1998).

Yen et al., "Antioxidative Activity and Scavenging Effects on Active Oxygen of Xylose-Lysine Maillard Reaction Products," J. Sci. Food Agric., 67:415-420 (1995).

Glycoprotein Monosaccharide Analysis Using High-Performance Anion-Exchange Chromatography with Pulsed Amperometric Detection (HPAE-PAD), Dionex, Technical Note 40, 6 pp. (1998).

Cargill Acidulants, "Proposal for making a "Substantial Equivalence" notification for Non-Shellfish Glucosamine Hydrochloride under Regulation (EC) No. 258/97 for the European Parliament and the Council of Jan. 27, 1997 concerning novel foods and novel food ingredients," Feb. 5, 2004.

Cargill, Incorporated, "Gras Notification for Regenasure™ Glucosamine Hydrochloride," Apr. 6, 2004.

Nikolaeva et al., "Preparation of glucosamine from shrimp shells, and its use in medicine," Tr. Vses. Nauchno Issled. Inst. Morsk. Rybn. Khoz Okeanogr., pp. 165-169 (1967) (Abstract).

Chen, George C. et al., "Improved Colorimetric Determination of Cell Wall Chitin in Wood Decay Fungi," Applied and Environmental Microbiology, vol. 46, No. 1, pp. 13-16 (Jul. 1983).

Nilsson, Kent et al., "Chitin as an indicator of the biomass of two wood-decay fungi in relation to temperature, incubation time, and media composition," Can. J. Microbiol., vol. 44, pp. 575-581 (1998).

Novikov, V. Yu., "Kinetics of formation of D-(+)- glucosamine in acid hydrolysis of chitin," Russian Journal (Sankt-Peterburg), vol. 72, No. 1, pp. 147-152 (1999).

Plassard, Claude S. et al., "Estimation of Mycelial Growth of Basidiomycetes by Means of Chitin Determination," Phytochemistry, vol. 21, No. 2, pp. 345-348 (1982).

Cao, G., "Preparation of Glucosamine Hydrochloride from Chitin," Journal: Huaxue Shijie, vol. 39, No. 5, pp. 250-253 (1998).

Ekbald, A. et al., "Determination of chitin in fungi and mycorrhizal roots by an improved HPLC analysis of glucosamine," Plant and Soil, vol. 178, pp. 29-35 (1996).

Hicks, R.E. et al., "A comparison of glucosamine and biovolume conversion factors for estimating fungal biomass," Oikos, vol. 42, pp. 355-360 (1984).

Novikov, V. Yu., "Kinetics of Formation of D(+)-Glucosamine by Acid Hydrolysis of Chitin," Russian Journal of Applied Chemistry, vol. 72, No. 1, pp. 156-161 (1999).

Ride, J.P. et al., "A rapid method for the chemical estimation of filamentous fungi in plant tissue," Physiol. Plant Pathol, vol. 2, pp. 7-15 (1972).

Schmitz, O. et al., "Quantification of vesicular-arbuscular mycorrhiza by biochemical parameters," J. Plant Physiol, vol. 139, pp. 106-114 (1991).

Office Action from the Canadian Intellectual Property Office for Canadian Patent Application No. 2,438,233, dated Apr. 7, 2009.

Office action dated Mar. 29, 2006 for U.S. Appl. No. 10/382,251, filed Mar. 5, 2003.

English Translation of JP2000281696, published Oct. 10, 2000.

Aiqin, Wang et al., "Preparation and Quality Analysis of N-(carboxymethyl) Chitosan," Chinese Journal of Biochemical Pharmaceutics, pp. 147-149 (1996) (English translated title and abstract).

Aiqin, Wang et al., "Studies on Preparation and Properties of Chitosan Membrane of Matrix," vol. 15, No. 1, pp. 49-51, 54 (1996) (English translated title and abstract).

An, Yanhua et al., "Phosphorus Wastewater Treatment Technology," Liaoning Chemical Industry, vol. 26, No. 4 (1997) (English translated title and abstract).

Anon., "Extraction Technology for Chitin" (not dated) (English translated title). This reference concerns chitin extraction technology.

Bafang, Li et al., "The Comparative Studies on Dietary Fibres in Diabetic Rats," Acta Nutrimenta Sinica, vol. 21, No. 1, pp. 59-64 (Mar. 1999) (English translated title and abstract).

Bangliang, Li et al., "The Preparation and Analysis of Low-molecular Weight Chitosan," Chinese Journal of Biochemical Pharmaceutics, vol. 20, No. 6, pp. 292-294 (1999) (English translated title and abstract).

"Biomacromolecules—An interdisciplinary journal focused at the interface of polymer science and the biological sciences," listing of articles contained therein, American Chemical Society, vol. 9, No. 7, 14 pages (Jul. 2008).

Bi, Jianwei et al., "Current Study Process on Clarification of Oral Formulations," Shandong Medical Industry, vol. 17, No. 3 pp. 25-26 (1998) (English translated title). The reference appears to concern chitin for use in medicinal preparations.

Bi, Yangeng, "Study on Factors Affecting Chitin Product Quality," Shaanxi Chemical Industry, No. 4, pp. 31-32 (1994) (English translated title). The reference appears to concern chitin properties and quality.

Bofen, Yan et al., "Effect of Microwave Radiation Energy on Chitosan Preparation and Properties," Food and Fermentation Industries, vol. 23, No. 2, pp. 39-41 (not dated) (English translated title and abstract).

Buhua, Qu et al., "Improvement of Chitin Preparation Technique," Chinese Journal of Biochemical Pharmaceutics, vol. 16, No. 2, pp. 63-65 (1995) (English translated title and abstract).

Cai, Jingping et al., "Study on Production of Amino Chitosan Oligosaccharide," Food Science, vol. 21, No. 9 pp. 21-24 (2000) (English translated title and abstract).

Cao, Genting, "Trial Preparation of Amino Glucosamine," *Chemical World*, pp. 250-253 (1998) (English translated title and abstract).

Under Seal Cargill Bound Notebook, Book No. 5667, 105 pages (May 20, 2003-Feb. 18, 2004).

Under Seal Cargill Research Notebook, Book No. 3568, 111 pages (May 4, 1999-Jan. 30, 2001).

Under Seal Cargill Research Notebook, Book No. 3654, 104 pages (May 16, 2002-Apr. 30, 2003).

Under Seal Cargill Research Notebook, Book No. 4209, 103 pages (Nov. 26, 2002-Apr. 17, 2003).

Under Seal Cargill Research Notebook Analytical Requests No. 1, Book No. 3646, 81 pages (Aug. 11, 1997-Jun. 13, 2002).

Under Seal Cargill Research Notebook BUP-2, Book No. 4235, 64 pages (Feb. 1, 2001-Feb. 19, 2002).

Under Seal Cargill Research Notebook GAP #1, Book No. 4237, 163 pages (Jan. 25, 2001-Jun. 4, 2001).

Under Seal Cargill Research Notebook Investigation & Troubleshooting No. 2, Book No. 3647, 86 pages (Sep. 2, 1997-Jun. 24, 2002).

Under Seal Cargill Research Notebook Method Development No. 2, Book No. 3160, 172 pages (Jan. 19, 1996-Mar. 6, 2002).

Under Seal Cargill Research Notebook Method Development No. 4, Book No. 3162, 150 pages (Jul. 30, 1996-Aug. 20, 2001).

Under Seal Cargill Research Notebook Method Development No. 5, Book No. 3842, 107 pages (Aug. 24, 1999-Apr. 8, 2002).

Under Seal Cargill Research Notebook Method Development No. 6, Book No. 4238, 9 pages (Jun. 22, 2001-Jun. 28, 2001).

Under Seal Cargill Research Notebook Production # 1, Book No. 3985, 131 pages (Apr. 15, 1999-Aug. 30, 1999).

Cargill's Opposition to Motion for Summary Determination of Invalidity of the '433 Patent by Respondent Nantong Foreign Trade Medicines & Health Products Co., Ltd. (dated Jun. 11, 2009).

Cargill's Response to Motion for Leave to File Reply to Cargill's Opposition to NFT's Motion for Summary Determination of Invalidity of the '433Patent by Respondent Nantong Foreign Trade Medicines & Health Products Co., Ltd. (dated Jun. 22, 2009).

Chang, Ke Liang B. et al., "HPLC Analysis of N-acetyl-chitooligosaccharides during the Acid Hydration of Chitin," *Journal of Food and Drug Analysis*, vol. 8, No. 2, pp. 75-83 (2000).

Changming, Ye et al., "Preparation Property and Application of Water-solubility Chitin Derivatives," *Comments & Reviews in C.I.*, pp. 5-10 (Nov. 1999) (English translated title and abstract).

Chaohui, Zhang, "Natural Macromolecular Compound: Chitin and Its Derivatives (Continued)," *G.X. Light Ind.*, pp. 15-17 (Apr. 1999) (English translated title). The reference appears to concern chitin and derivatives of chitin.

Chen, Chunxin et al., "A Study on Preparation of Chitosan and its Derivatives," *Hunan Chemical Industry*, vol. 29, No. 3, pp. 12-15 (Jun. 1999) (English translated title and abstract).

Chen, Ling-yun et al., "Structure-antimicrobial ability relationship of Carboxymethyl Chitosan," *J. Wuhan Univ. (Nat. Sci. Ed.)*, vol. 46, No. 2, pp. 191-194 (Apr. 2000) (English translated title and abstract).

Chen, Lusheng, "Study on Preparation Parameters of Completely Soluble Chitosan," *Chemistry*, No. 8 pp. 48-50 (1998) (English translated title). The reference appears to concern chitosan and chitin.

Chen, Yuru et al., "Preparation of Chitosan and Production of Hair Styling Gel," *Chemical World*, No. 4, pp. 187-189 (1996) (English translated title and abstract).

Commission Investigative Staff's Response to Respondent NFT's Motion for Summary Determination of Invalidity of the '433 Patent (dated Jun. 12, 2009).

Connell, P.J. et al., "Improved Techniques in the Measurement of Amino Acids and Amino Sugars in Rumen Anaerobic Fungi," *Proc. Nutr. Soc. Aust.*, vol. 12, pp. 92-95 (1987).

Ding, Ming et al., "Study on Preparation of Chitosan Micro Spheres," *Chemical World*, No. 12, pp. 636-640 (1998) (English translated title and abstract).

Dinghe, Zhu, "Application of Chitin/Chitosan and its derivative," *Journal of Shaoguan University (Natural Science)*, vol. 19, No. 3, pp. 147-150 (Jun. 1998) (English translated title and abstract).

Dongmei, Yang et al., "The Exploration and Application of the Biological Materials—Chitin/Chitosan," *Chemical Industry and Engineering*, vol. 16, No. 6, pp. 335-340, 371 (Dec. 1999) (English translated title and abstract).

Du, Weicheng et al. "Study on Edible Zein Complex Film," *CFI*, vol. 4, No. 4, pp. 22-26 (Apr. 1997) (English translated title). The reference appears to concern chitin.

Einbu, Aslak et al., "Characterization of Chitin and Its Hydrolysis to GlcNAc and GlcN," *Biomacromolecules*, vol. 9, No. 7, pp. 1870-1875 (2008).

Eitelman, Stephen J. et al., "Decomposition.Reactions of Amino Sugars: The Dehydration of 2-Amino-2-Deoxy-D-Glucose," *Carbohydrate Research*, vol. 77, pp. 205-211 (1979).

Falk, Michael et al., "Studies on Chitan (($\beta$-(1→4),-Linked 2-Acetamido-2-Deoxy-D-Glucan) Fibers of the Diatom Thalassiosira Fluviatilis Hustedt" *Canadian Journal of Chemistry*, vol. 44, pp. 2269-2281 (1966).

Fan, Jian-Qiang et al., "Comparison of Acid Hydrolytic Conditions for Asn-Linked Oligosaccharides," *Analytical Biochemistry*, vol. 219, pp. 375-378 (1994).

Fengqi, Lu et al., "Studies on Preparation of Low-Molecular-Weight Chitosan," *Chinese Journal of Biochemical Pharmaceutics*, vol. 18, No. 4, pp. 178-180 (1997) (English translated title and abstract).

Gu, Guiwen et al., "Medical Application of Chitin and Chitosan," *Heilongjiang Medical Journal*, vol. 9, No. 4, pp. 184-185 (1996) (English translated title and abstract).

Guo, Zhenchu, "Study Progress on Chitin," *China Surfactant*, Detergent & Cosmetics, No. 2, pp. 29-32 (1997) (English translated title and abstract).

Guoqi, Wu et al., "The Preparation and Application of Oligochitosan," Abstract Only, pp. 14 (1996).

He, Pingfen, "Chitin/Chitosan, the Sixth Life Element for Human Body," *China Public Health*, vol. 14, No. 3, pp. 187-189 (1998) (English translated title). The reference appears to concern properties of chitin.

He, Xiaojin et al., "Study on Synthesis and Adsorption Properties to Metal of Chitosan Chelated Resins," *Ion Exchange and Adsorption*, vol. 16, No. 1, pp. 47-53 (2000) (English translated title and abstract).

Hezhong, Liu et al., "Chitin Plant Growth Regulator Applying to the Maize," *Natural Product Research and Development*, vol. 8, No. 4, pp. 90-92 (1995) (English translated title and abstract).

Hong, Liu et al., "Recent Applications in the Research of Chitosan," *J. of Huaihai Inst. of Tech. (Nat. Sci.)*, vol. 5, No. 2, pp. 66-69 (Dec. 1996) (English translated title and abstract).

Hu, Zhong-Ming et al., "Thermotropic Phase Transition of Liquid Crystalline Solution of Chitosan/Dichloroacetic Acid," *Chemical Journal of Chinese Universities*, vol. 20, No. 1, pp. 153-155 (Jan. 1999) (English translated title and abstract).

Huang, Wenqian et al., "New Progress on Nature Macromolecular Chitin/Chitosan," *Chemical Industry and Engineering Progress*, No. 6, pp. 23-25 (1998) (English translated title and abstract).

Huang, Ziyang et al., "Application Summary of Chitin and its Derivatives," *Fujian Chemistry and Industry*, No. 4, pp. 9-15 (1998) (English translated title and abstract).

Jian, Cao et al., "Study on Chitin and Chitosan of *Aspergillus Niger*," vol. 22, No. 4, pp. 200-203 (1995) (English translated title and abstract).

Jiang, Tingda, *Chitin*, Chemical Industry Press, Beijing, 2003. 1 ISBN 7-5025-3998-0 (not dated) (English translated title). The reference appears to concern chitin.

Jiang, Tingda, *Chitosan*, Chemical Industry Press (not dated) (English translated title). The reference appears to concern chitin and chitosan.

Jiang, Tingda, *Chitosan*, Chemical Industry Press, Beijing, 2000 ISBN 7-5025-3143-0 (not dated) (English translated title). The reference appears to concern chitin and chitosan.

Jie, Luo et al., "Application of Modified Chitin and Chitosan in Food," pp. 39-40, 54 (Feb. 1999) (English translated title and abstract).

Jiheng, Li et al., "Studies on Preparation of Carboxymethylchitosan," *Chinese Journal of Biochemical Pharmaceutics*, pp. 175-177 (Apr. 21, 2000) (English translated title and abstract).

Jihua, Yu et al., "Studies on Chemical Modification and application of Chitin and Chitosan," pp. 28-32 (Mar. 1997) (English translated title and abstract).

Jinyun; Wang et al., "Preparation of Chitin and Chitosan," *Journal of Hebei Institute of Chemical Technology and Light Industry*, vol. 16, No. 1, pp. 48-52, 62 (1995) (English translated title and abstract).

Jisheng, Yang, "Application of Carboxy Methyl Chitosan in Cosmetics," *Fine Chemicals*, vol. 14, pp. 62-64 (1997) (English translated title and abstract).

Jisheng, Yang, "Preparation and Application of Chitin and its Derivatives," *Journal of Yangzhou Institute of Technology*, vol. 7, No. 1, pp. 64-68 (Jun. 1995) (English translated title and abstract).

Johnson, Bruce R. et al., "Occurrence and Inhibition of Chitin in Cell Walls of Wood-Decay Fungi," *Holzforschung*, vol. 37, pp. 255-259 (1983).

Kirchman, David L., "Hydrolysis and mineralization of chitin in the Delaware Estuary," *Aquatic Microbial Ecology*, vol. 18, pp. 187-196 (Aug. 9, 1999).

Kralovec, Jaroslav A. et al., "Glucosamine Production and Health Benefits," in *Marine Nutraceuticals and Functional Foods*, Ch. 8, pp. 197-227 (2008).

Li, Shupin et al., "Safety and Physiological Activity of Chitosan," *Shandong Food Science and Technology*, No. 5, pp. 22-23 (1999) (English translated title and abstract).

Li, Zhi et al., "Antimicrobial Activity of O-Carboxymethyl-Chitosan," *China Surfactant Detergent & Cosmetics*, vol. 3, pp. 10-11 (Jun. 2000) (English translated title and abstract).

Lin, Youwen et al., "Medical Applications of Chitin and its Derivatives," *Journal of Fujian Medical University*, vol. 33, No. 2, pp. 226-228 (Jun. 1999) (English translated title). The reference appears to concern medicinal uses of chitin.

Lin, Youwen et al., "Preparation of Carboxymethyl Chitosan by Ultrasonic Radiation," *Ion Exchange and Adsorption*, vol. 16, No. 1, pp. 54-59 (2000) (English translated title and abstract).

Liu, Hengsheng et al., "Preparation and Application of Chitin and Chitosan," *Application Technology*, No. 7 (1998) (English translated title). The reference appears to concern chitin preparation processes.

Liu, Hong et al., "Study on Preparation Process of Soluble Chitin with High Viscosity," *Chemical World*, No. 6, pp. 303-306 (1994) (English translated title and abstract).

Liu, Nan et al., "Extraction Technology for Chitin," pp. 14 (unidentified publ. source; not dated) (English translated title). The reference appears to concern extraction of chitin.

Liu, Xing et al., "Chemical Methods to Develop Chitosan Products," *Fujian Chemical Industry*, No. 3 pp. 20-24 (1994) (English translated title and abstract).

Liwei, Zhang et al., "The Study on Preparation and Decolorization of Glucosamine Hydrochloride," *China Academic Journal Electronic Publishing House*, vol. 2, pp. 84-86 (1999) (English translated title and abstract).

Longfa, Jiang et al., "Immobilized Glucoamylase E.C.3.2.1.3 with Hollow Globe Chitosan," vol. 12, pp. 638-641 (1999) (English translated title and abstract).

Maley, Frank et al., "Synthesis of N-Substituted Glucosamines and their Effect on Hexokinase," *The Journal of Biological Chemistry*, pp. 765-773 (Oct. 1954).

Munir, Erman et al., "An Inhibitory Effect of Acetate Added to the Culture on Growth of Wood Rotting Basidiomycetes," *Proceedings of the 6th International Wood Science Symposium*, pp. 405-410 (Aug. 29-31, 2005).

Na, Haiqiu et al., "Nature, Preparation, and Application of Chitosan," *Liaoning Chemical Industry*, vol. 26, No. 4, pp. 194-195 (Jul. 1997) (English translated title and abstract).

Nan, Li et al., "Preparation of D-Glucosamine Hydrochloride," *Journal of China Pharmaceutical University*, vol. 28, No. 1, pp. 56-58 (1997) (English translated title and abstract).

Neng, Zhou et al., "A One-Step Method for the Preparation of Chitosan with Microwave Irradiation," *Journal of Guangxi Normal University*, vol. 16, No. 2, pp. 54-58 (Jun. 1998) (English translated title and abstract).

Nikolayeva, N.E. et al., "Production of Glucosamine from Shrimp Shells and Its Use in Medicine," *Ministry of Fisheries of the USSR—All-Union Scientific and Research Institute of Marine Fisheries and Oceanography (VNIRO)*, vol. LXIII, 7 pages (1967).

Ningwen, Tai et al., "Preparation of Chitosan from Silkworm Pupae and Using Chitosan as Support of Enzyme Immobilization," *Natural Product Research and Development*, vol. 9, No. 2, pp. 48-52 (1996) (English translated title and abstract).

Notice of Commission Determination Not to Review an Initial Determination Granting a Joint Motion to Terminate the Investigation as to Respondent DNP International, Inc. Based on a Consent Order; Issuance of Consent Order (dated Jul. 30, 2009).

Notice of Commission Determination Not to Review an Initial Determination Granting Complainant's Unopposed Motion to Withdraw its Complaint and Terminate the Investigation as to Two Respondents (dated Jul. 28, 2009).

Notice of Commission Determination to Review an Initial Determination Granting a Joint Motion to Terminate the Investigation as to Respondent Ethical Naturals, Inc. from the Investigation Based Upon a Settlement Agreement; Briefing Schedule (dated Aug. 24. 2009).

Office Action from the European Patent Office for European Patent Application No. 07753854.4, dated Aug. 3, 2009.

Office action from the U.S. Patent and Trademark Office for U.S. Appl. No. 11/394,981, dated Aug. 24, 2009.

Office action from the U.S. Patent and Trademark Office for U.S. Appl. No. 11/395,013, dated Oct. 14, 2009.

Order No. 20: Denying Respondent NFT's Motion for Summary Determination of Invalidity (dated Jun. 22, 2009).

Peigen, Zhou et al., "Preparation and some properties of glucosamine hydrochloride," *Journal of Fisheries of China*, vol. 24, No. 1, pp. 76-80 (Feb. 2000) (English translated title and abstract).

Qian, Hesheng et al., "Study on Preparation and Solubility of Amino Glucosamine," *Chemical World*, No. 2 pp. 75-78 (1994) (English translated title and abstract).

Qin, Cai-qin et al., "Prediction and Control of Extent of Deploymerization of Chitosan by Hydroperoxide," *J. Wuhan Univ. (Nat. Sci. Ed.)*, vol. 46, No. 2, pp. 195-198 (Apr. 2000) (English translated title and abstract).

Rajderkar, N.R., "Decay of Wood by Alternaria and Penicillium and Chief Methods of Control," *Mycopathologia*, vol. 30, No. 2, pp. 149-151 (Jun. 1966).

Respondent Nantong Foreign Medicines & Health Products Co., Ltd.'s and Respondent Tiancheng International Inc.'s Notice of Prior Art (dated Jun. 5, 2009).

Under Seal Respondent Nantong Foreign Trade Medicines & Health Products Co., Ltd.'s Amended and/or Supplemental Responses and Objections to Complainant Cargill's First Set of Interrogatories to Respondent Nantong Foreign Trade Medicines & Health Products, Co., Ltd (Nos. 2, 4-9, 12-13, 17, 19-26, 28-30, 33-41, 43, 45-46, 49-52) (dated Jun. 2, 2009).

Respondent NFT's Motion for Leave to File Reply to Complaint Cargill, Incorporated's Opposition to NFT's Motion for Summary Determination of Invalidity of the '433 Patent (dated Jun. 18, 2009).

Respondent NFT's Motion for Summary Determination of Invalidity of the '433 Patent Based on Prior Art (dated May 29, 2009).

Respondent NFT's Request to Withdraw its Motion for Summary Determination of Invalidity of the '433 Patent and Non-Opposition to Cargill's Motion to Withdraw Complaint and Terminate Investigation as to NFT and Tiangcheng International, Inc. (dated Jun. 23, 2009).

Restriction Requirement from the U.S. Patent and Trademark Office for U.S. Appl. No. 11/394,981, dated May 21, 2009.

Restriction Requirement from the U.S. Patent and Trademark Office for U.S. Appl. No. 11/395,013, dated Jun. 2, 2009.

Rongjun, "Dietary Fibers Can Give You Healthy and Beautiful Skin," *China Health*, No. 5 (1996) (English translated title). The reference appears to concern chitin in food supplements.

Ross, W., "The Origin of the Glucosamine Obtained in the Hydrolysis of *Boletus edulis*," *Glucosamine from Boletus edulis*, Chap. XXIX, pp. 313-319 (1915).

Ruiquan, Fan et al., "Preparation of Chitosan and Its Flocculation," *Journal of Fuzhou University (Natural Science)*, vol. 23, No. 1, pp. 71-75 (Feb. 1995) (English translated title and abstract).

Ruiz-Herrera, J., "Biosynthesis of (β-glucans in fungi," *Antonie van Leeuwenhoek*, vol. 60, pp. 73-81 (1991).

Rupley, J.A., "The Hydrolysis of Chitin by Concentrated Hydrochloric Acid, and the Preparation of Low-Molecular-Weight Substrates for Lysozyme," *Biochimica et Biophysica Acta*, vol. 83, No. 3, pp. 245-255 (Nov. 1, 1964).

Sandula, J. et al., "Microbial (1 → 3)-β-D-glucans, their preparation, physico-chemical characterization and immunomodulatory activity," *Carbohydrate Polymers*, vol. 38, pp. 247-253 (1999).

Shabrukova, Nataliya V. et al., "Research of Acid Hydrolyses of Chitin-Glucan and Chitosan-Glucan Complexes," *Chemistry and Computational Simulation. Butlerov Communications*, vol. 2, No. 8, pp. 57-59 (2002).

Shahidi, Fereidoon et al., "Chitin, Chitosan, and Co-Products: Chemistry, Production, Applications, and Health Effects," in *Advances in Food and Nutrition Research*, vol. 49, pp. 93-135 (2005).

Shan, Hu et al., "Study on Extraction Process of Chitin and Chitosan," *Food Science*, vol. 18, No. 10, pp. 14-15, (1997) (English translated title). The reference appears to concern processes for extraction of chitin.

Shao, Jian et al., "Biomedical Application of Chitin and Chitosan," *Journal of Nantong Medical College*, vol. 17, No. 1, pp. 145-146 (1997) (English translated title). The reference appears to concern uses for chitin.

Shen, Eran, "Magic Chitin and Chitosan," *Medicines and Men*, vol. 22, p. 87 (Mar. 1999) (English translated title). The reference appears to concern chitin uses.

Sheng, Chen et al., "Preparation of Chitosan Complex with Zinc," *Chinese Journal of Applied Chemistry*, vol. 15, No. 4, pp. 65-67 (Aug. 1998) (English translated title and abstract).

Sheng, Chen et al., "Study on Chitosan-immobilized Cellulase," *Prog. Biochem. Biophys.*, vol. 23, No. 3, pp. 250-254 (1996) (English translated title and abstract).

Sheng, Chen et al., "The Technological Condition of Preparing Chitosan from Five Materials," vol. 13, No. 4, pp. 54-57 (1996) (English translated title and abstract).

Song, Baozhen, "Chitin, Chitosan and Our Health," *Fine and Special Chemicals*, No. 21, pp. 11-12 (1999) (English translated title). The reference appears to concern chitin uses.

Subramanyam, C. et al., "An enzymic method for the determination of chitin and chitosan in fungal cell walls," *J. Biosci.*, vol. 12, No. 2, pp. 125-129 (Jun. 1987).

Tan, Zhiying et al., "Processing Technology and Application of Chitosan," *Development of Agricultural and Livestock Products*, No. 9, pp. 3-5 (1999) (English translated title and abstract).

Tingda, Jiang et al., "Study on the Adsorption Characteristics of Crosslinked Chitosan for Amino Acids," *Ion Exchange and Adsorption*, vol. 10, No. 2, pp. 127-133 (1994) (English translated title and abstract).

Under Seal Transcription of Deposition of John Andrew Bohlmann with Exhibits 1-19 (dated Jun. 12, 2009).

Under Seal Transcription of Deposition of Ki-Oh Hwang with Exhibits 1-6 (dated Jun. 16, 2009).

Under Seal Transcription of Deposition of James Steinke with Exhibits 1-11 (dated Jun. 18, 2009).

Under Seal Transcription of Deposition of James Trinkle with Exhibits 1-10 (dated Jun. 19, 2009).

Wang, Aiqin et al., "Study Progress on Application of Nature Macromolecular Material Chitosan," *New Chemical Materials*, No. 9, pp. 9-12 (1994) (English translated title and abstract).

Wang, Aiqin, "Denaturing of Chitin and Chitosan and its Application Prospect," *Applicable Technology Market*, No. 2, pp. 11-12 (1997) (English translated title and abstract).

Wang, Chengxian, "Development of Green Edible Packages for Food," *China Packaging Industry*, vol. 5, No. 10, pp. 10-11 (1997) (English translated title). The reference appears to concern chitin uses.

Wang, Chunxia, "Application of Chitosan on Absorptive Extraction and Isolation of Enzymes," *Hebei Chemical Industry*, No. 1, pp. 33-34 (1998) (English translated title). The reference appears to concern chitin.

Wang, Shikui et al., "Preparation and Chemical and Physical Properties of Amino Chitosan Oligosaccharide," *Chemical World*, No. 4, pp. 192-195 (1994) (English translated title and abstract).

Wang, Yueying, "Development and Applications of Chitin and its Derivatives," *Gangsu Light and Textile Technology*, No. 4, pp. 35-36 (1997) (English translated title and abstract).

Wei, Li et al., "Study on the Chemical Quantitative Analysis of Hyaluronic Acid," *Chinese Journal of Biochemical Pharmaceutics*, vol. 15, No. 2, pp. 96-99 (1994) (English translated title and abstract).

Wei, Xiyu et al., "Preliminary Study on Preparation of N, O-carboxymethyl Chitosan and its Effects on Storage Life of Strawberries," *Marine Science*, No. 2, pp. 3-5 (1998) (English translated title). The reference appears to concern chitosan uses.

Wen, Lu, "Dietary Fibers and their New Production Methods," *Technology Today*, No. 8, p. 5 (1998) (English translated title). The reference appears to concern production of chitin products.

Wenbo, Yang et al., "Purification and Properties of Chitinase from *Streptomyces* Sp. S01," vol. 24, No. 2, pp. 88-91 (1997) (English translated title and abstract).

Wenqian, Huang, "Properties and Applications of Chitin and Chitosan," *New Technology Domestic and International*, Abstract Only, pp. 40 (Jun. 1998) (English translated title and abstract).

Wenshui, Xia et al., "Recent Progress in the Research of Chitin/Chitosan Hydrolases," pp. 31-35 (Feb. 1997) (English translated title and abstract).

Wenshui, Xia et al., "Stability and Preparation of D-Glucosamine Hydrochloride," *Journal of Wuxi University of Light Industry*, vol. 16, No. 4, pp. 29-33 (1997) (English translated title and abstract).

Wu, Di et al., "Study on Mild Hydrolysis of Chitosan for Producing Glucosamine-hydrochloride," vol. 12, pp. 644-646 (2001) (English translated title and abstract).

Wu, Guoqi et al., "Preparation and Application of Chitosan-oligosaccharides," *Journal of Jiangsu Institute of Petrochemical Technology*, vol. 8, No. 2 pp. 29-31 (May 1996) (English translated title and abstract).

Wu, Jian-min, "Determination of Mean Relative Molecular Mass of Chitosan-oligosaccharide by Photometric Analysis," vol. 6, pp. 293-295 (2001) (English translated title and abstract).

Wu, L. et al., "Chromatographic Estimation of Fungal Mass in Plant Materials," *Phytopathology*, vol. 65, pp. 1032-1034 (Sep. 1975).

Xia, CHenJie et al., "Study on the Relationship between the Emulsification and the Structure of 6-O-CM-Chitosan," *China Surfactant Detergent & Cosmetics*, vol. 6, pp. 1-4, (Dec. 1999) (English translated title and abstract).

Xiaoqin, Fu et al., "A Kind of Fiber Formating Material with Abundant Source-Chitin-The Structure of Chitin," *Guangdong Chemical Fiber*, pp. 22-25 (Sep. 1996) (English translated title and abstract).

Xu, Jiachao et al., "Preparation Process of Chitin Powder," *Marine Science*, p. 34 (not dated) (English translated title). The reference appears to concern chitin processes.

Xu, Jiachao et al., "Study on Preparation Parameters of Chitosan Sulfate," *Marine Science*, pp. 2-4 (1994) (English translated title).

Xu, Jian et al., "Biological and Medical Application of Nature Macromolecular Chitin/Chitosan," *University Chemistry*, vol. 9, No. 3, pp. 22-25 (Jun. 1994) (English translated title). The reference appears to concern chitin uses.

Xu, Junyi, "Is 2000s the Century of Chitin?" *China Science and Technology Information*, No. 12, p. 27 (not dated) (English translated title). The reference appears to concern chitin uses.

Yamaoka, Futoshi et al., "Acid Degradation of Amino-monosaccharides and Amino-polysaccharides," *Agric. Biol. Chem.*, vol. 52, No. 8, pp. 2113-2114 (1988).

Yang, Yumin, "Medical Application of Chitin and its Derivatives," *Transportation Medicine*, vol. 10, No. 1, pp. 130-131 (1996) (English translated title). The reference appears to concern chitin uses.

Yankun, Zhang et al., "The Preparation and Applications of Chitin, Chitosan and their Derivatives," *China Surfactant Detergent & Cosmetics*, pp. 36-40 (Aug. 1998) (English translated title and abstract).

Yanming, Dong et al., "A Novel Family of Liquid Crystalline Biological Macromolecules—Chitin and Its Derivatives," pp. 48-56 (Dec. 1999) (English translated title and abstract).

Yanming, Dong et al., "Chitin-a Novel Kind of Liquid Crystalline Polysaccharide," *Progress in Chemistry*, vol. 11, No. 4, pp. 416-428 (Nov. 1999) (English translated title and abstract).

Yanming, Dong et al., "Preparation and Characterization of Benzoylchitosan—A New Liquid Crystalline Polymer," *Polymer Materials Science and Engineering*, vol. 15, No. 6, pp. 161-163 (Nov. 1999) (English translated title and abstract).

Yanming, Dong et al., "Structure studies on solution casting film of chitosan and its derivatives," No. 4, pp. 24-29 (1997) (English translated title and abstract).

Yanming, Dong et al., "Texture Studies of Liquid Crystalline Butyryl Chitosan," *Journal of Functional Polymers*, vol. 11, No. 1, pp. 87-90 (Mar. 1998) (English translated title and abstract).

Yimin, Qin et al., "Methods of Immobilization of Enzymes on Chitosan," *Journal of Guangxi University*, vol. 23, No. 2, pp. 124-126 (Jun. 1998) (English translated title and abstract).

Yu, Zidong et al., "Study on Preparation of Carboxmethyl Chitosan," *Guangxi Light Industry*, No. 3, pp. 17-19 (1998) (English translated title and abstract).

Yufang, Pan et al., "Applicaton of Chitin and Chitosan in the Preparation of Drugs," *Acad J GCP*, vol. 13, No. 3, pp. 177-179 (1997) (English translated title and abstract).

Yuguang, Du et al., "Filtration of Beauveria Bassiana with High-Yield Chitosanase and its Activity of Hydrolyzing Chitosan," pp. 24-27 (1999) (English translated title and abstract).

Yun, Qi et al., "Preparation and applications of chitin and its derivatives," pp. 15-20 (1995) (English translated title and abstract).

Yuping, Huang, "Study on the Application of Chitin and Chitosan," *Journal of Shaoguan University (Natural Science)*, vol. 16, No. 2, pp. 128-132 (Jun. 1995) (English translated title and abstract).

Zhang, Qichang et al., "Study on Clarification of Emblica Juice by Chitosan," *Food Science*, vol. 16, No. 2, pp. 26-28 (not dated) (English translated title and abstract).

Zhang, Qiuhua et al., "Preparation and Application of Soluble Derivatives of Chitin," *Jiangsu Chemical Industry*, vol. 22, No. 1, pp. 6-7 (1994) (English translated title and abstract).

Zhang, Qiuhua et al., "Study on Moisture Retention Capacity of Soluble Chitin Derivatives," *China Surfactant, Detergent and Cosmetics*, No. 3, pp. 13-15 (1996) (English translated title and abstract).

Zhang, Xi et al., "On the Polymerization Coating Performance of Chemically Modified Materials for the Chitin and Chitosan," *J. Wuhan Univ. (Nat. Sci. Ed.)*, vol. 45, No. 2, pp. 181-184 (Apr. 1999) (English translated title and abstract).

Zhang, Yankun, "Application of Chitin and Chitosan in Food," *The Food Industry, Special Issue of Additives and Adjuvants*, No. 3, pp. 9-11 (1998) (English translated title and abstract).

Zhao, Ji-lun et al., "The Preparation of Chitosan from waste mycelia of *Asper. niger*," *Industrial Microbiology*, vol. 29, No. 2, pp. 33-37 (Jun. 1999) (English translated title and abstract).

Zhaoxia, Wu, "The Chemical Reaction of Chitin and Applications of Chitosan," *Guangdong Chemical Fiber*, pp. 12-18 (Dec. 1997) (English translated title and abstract).

Zheng, Hua et al., "Structure and Preparation of Chitosan/Poly(vinyl alcohol) Blend Fibers," *J. Wuhan Univ. (Nat. Sci. Ed.)*, vol. 46, No. 2, pp. 187-190 (Apr. 2000) (English translated title and abstract).

Zhen-nan, Liu, "Preparation and Property of Chitin Derivant," *Journal of Guangxi University for Nationalities*, vol. 1, No. 1, pp. 92-95 (Jun. 1995) (English translated title and abstract).

Zhou, Ri-you, "Production Application and Development of Citric Acid in China," *Jiangsu Chemical Industry*, vol. 29, No. 5, pp. 10-13 (Oct. 2001) (English translated title and abstract).

Zhou, Tao et al., "Study of Preparation and Characterization of Trypsin Immobilized to Chitosan," *Journal of Ningbo University*, vol. 12, No. 1, pp. (Mar. 1999) (English translated title and abstract).

Zongshun, Cao et al., "Studies on Preparation of Chitosan Films and It's Stability," *Chinese Journal of Biochemical Pharmaceutics*, pp. 178-179 (Apr. 16, 1995) (English translated title and abstract).

Office Action from the European Patent Office for European Patent Application No. 07753949.2, dated Apr. 4, 2010.

Aldrich, Catalog Hand book of Fine Chemicals, p. 756 (1996).

Alonso, I. et al., "Determination of the Degree of Acetylation of Chitin and Chitosan by Thermal Analysis," *Journal of Thermal Analysis*, vol. 28, pp. 189-193 (1983).

Arcidiacono, S. et al., "Molecular Weight Distribution of Chitosan isolated from *Mucor rouxii* under Different Culture and Processing Conditions," *Biotechnology and Bioengineering*, vol. 39, pp. 281-286 (1992).

Atrih, A. et al., "Analysis of Peptidoglycan Structure from Vegetative Cells of *Bacillus subtilis* 168 and Role of PBP 5 in Peptidoglycan Maturation," *Journal of Bacteriology*, vol. 181, No. 13, pp. 3956-3966 (Jul. 1999).

Bartnicki-Garcia, S., "Cell Wall Chemistry, Morphogenesis, and Taxonomy of Fungi," *Chemistry of Fungal Cell Wall*, pp. 87-108 (1968).

Benjakul, S. et al., "Improvement of Deacetylation of Chitin from Black Tiger Shrimp (*Penaeus monodon*) Carapace and Shell," *ASEAN Food Journal*, vol. 9, No. 4, pp. 136-140 (1994).

Beri, R., et al., "Characterization of Chitosans via Coupled Size-Exclusion Chromatography and Multiple-Angle Laser Light-Scattering Technique," *Carbohydrate Research*, vol. 238, pp. 11-26 (1993).

Carlson, T. et al., "Chitin/Chitosan Extraction from *A. niger* Mycelium," *Cargill Central Research*, 16 pages (Aug. 1997).

"Chitin/Chitosan Specifications," *Biopolymer Engineering, Inc.*, http://www.biopolymer.com/spec.htm, 1 page (Date printed Mar. 4, 1999).

Davies, D., et al., "Determination of the Degree of Acetylation of Chitin and Chitosan," *Methods in Enzymology*, vol. 161, Part B, pp. 442-446 (1988).

Deal, C. et al., "Nutraceuticals as Therapeutic Agents in Osteoarthritis. The Role of Glucosamine, Chondroitin Sulfate, and Collagen Hydrolysate," *Osteoarthritis*, vol. 25, No. 2, pp. 379-395 (May 1999).

Domszy, J. et al., "Evaluation of Infrared Spectroscopic Techniques for Analyzing Chitosan," *Makromal. Chem.*, vol. 186, pp. 1671-1677 (1985).

Farkas, V., "Fungal Cell Walls: Their Structure, Biosynthesis and Biotechnological Aspects," *Acta Biotechnol.*, vol. 10, No. 3, pp. 225-238 (1990).

Ferrer, J., "Acid Hydrolysis of Shrimp-Shell Wastes and the Production of Single Cell Protein from the Hydrolysate," *Bioresourcc Technology*, vol. 57, pp. 55-60 (1996).

Fleet, G. et al., "17 Fungal Glucans—Structure and Metabolism," *Encyclopedia of Plant Physiology*, vol. 13B, New Series, pp. 416-440 (1981).

Gassner, G. et al., "Teichuronic Acid Reducing Terminal $N$-Acetylglucosamine Residue Linked by Phosphodiester to Peptidoglycan of *Micrococcus luteus*," *J. Bacteriol.*, vol. 172, No. 5. pp. 2273-2279 (May 1990).

"Glucosamine Hydrochloride," *Pharmacopeial Forum*, vol. 26, No. 5, pp. 1449-1450 (Sep.-Oct. 2000).

Gobin, P. et al., "Structural Chemistry of Fungal Polysaccharides," pp. 367-417 (1968).

Jacobson, R., "Berichte der Deutschen Chemischen Gesellschaft," pp. 2192-2200 (1898) (German).

Johnston, I., "The Composition of the Cell Wall of *Asperigillus niger*," *Biochem. J.*, vol. 96, pp. 651-658 (1965).

Kimura, K. et al, "Determination of the Mode of Hydrolysis of Chitooligosaccharides by Chitosanase Derived from *Aspergillus Oryzae* by Thin Layer Chromatography," *Chemistry Letters*, pp. 223-226 (1992).

Kurita, K., "Controlled Functionalization of the Polysaccharide Chitin," *Prog. Polym. Sci.*, vol. 26, pp. 1921-1971 (2001).

Kurita, K. et al., "Studies on Chitin, 3, Preparation of Pure Chitin, Poly($N$-acetyl-D-glucosamine), from the Water-Soluble Chitin," *Makromal. Chem.*, vol. 178, pp. 2595-2602 (1977).

Kurita, K. et al., "Studies on Chitin, 4, Evidence for Formation of Block and Random Copolymers of $N$-Acetyl-D-glucosamine and D-Glucosamine by Hetero- and Homogeneous Hydrolyses," *Makromol. Chem.*, vol. 178, pp. 3197-3202 (1977).

Maghami, G. et al., "Evaluation of the Viscometric Constants for Chitosan," *Makromol. Chem.*, vol. 189, pp. 195-200 (1988).

Maitre, N. et al., "Primary T-Cell and Activated Macrophage Response Associated with Tumor Protection Using Peptide/Poly-$N$-Acetyl Glucosamine Vaccination," *Clinical Cancer Research*, vol. 5, pp. 1173-1182 (May 1999).

Mima, S. et al., "Highly Deacetylated Chitosan and Its Properties," *Journal of Applied Polymer Sciences*, vol. 28, pp. 1909-1917 (1983).

Muzzarelli, R. et al., "Chelating, Film-Forming, and Coagulating Ability of the Citosan-Glucan Complex from *Aspergillus niger* Industrial Wastes," *Biotechnology and Bioengineering*, vol. XXII, pp. 885-896 (1980).

Nanjo, F. et al., "Purification, Properties, and Transglycosylation Reaction of β-N-Acetylhexosaminidase from *Nocardia orientalis*," *Agric. Biol. Chem.*, vol. 54, No. 4, pp. 899-906 (1990).

Nanjo, F. et al., "Purification and Characterization of an Exo-β-D-glucosaminidase, a Novel Type of Enzyme, from *Nocardia orientalis*," *The Journal of Biological Chemistry*, vol. 265, No. 17, pp. 10088-10094 (Jun. 15, 1990).

Nanjo, F. et al., "Enzymatic Method for Determination of the Degree of Deacetylation of Chitosan," *Analytical Biochemistry*, vol. 193, pp. 164-167 (1991).

Nikolaeva et al., CAPLUS Abstract, AN 1968:62461 (1968).

Nguyen, T. et al., "Composition of the Cell Walls of Several Yeast Species," *Abstract*, vol. 50, No. 2, pp. 206-212 (1998).

Niola, F. et al., "A Rapid Method for the Determination of the Degree of N-acetylation of chitin-chitosan samples by acid hydrolysis and HPLC," *Carbohydrate Research*, vol. 238, pp. 1-9 (1993).

No, H. et al. "Preparation and Characterization of Chitin and Chitosan—A Review," *Journal of Aquatic Food Product Technology*, vol. 4, No. 2, pp. 27-51 (1995).

Nogawa, M. et al., "Purification and Characterization of Exo-β-D-Glucosaminidase from a Cellulolytic Fungas, *Trichoderma reesei* PC-3-7," *Appl. Environ. Microbiol.*, vol. 64, No. 3, pp. 890-895 (Mar. 1998).

Novikov, V. et al., "Synthesis of D(+)-Glucosamine Hydrochloride," *Russian Journal of Applied Chemistry*, vol. 70, No. 9, pp. 1467-1470 (1997).

Ottoy, M. et al., "Preparative and Analytical Size-exclusion Chromatography of Chitosans," *Carbohydrate Polymers*, vol. 31, pp. 253-261 (1996).

Pelletier, A. et al., "Chitin/Chitosan Tranformation by Thermo-Mechano-Chemical Treatment Including Characterization by Enzymatic Depolymerization," *Biotechnology and Bioengineering*, vol. 36, pp. 310-315 (1990).

Rege, P. et al. "Chitosan Processing: Influence of Process Parameters During Acidic and Alkaline Hydrolysis and Effect of the Processing Sequence on the Resultant Chitosan's Properties," *Carbohydrate Research*, vol. 321, Nos. 3-4, pp. 235-245 (Oct. 15, 1999).

Roberts, G. et al., "Determination of the Viscomtric Constants for Chitosan," *Int. J. Biol.*, vol. 4, pp. 374-377 (Oct. 1982).

Rokem, J. et al., "Degradation of Fungal Cell Walls Taking into Consideration the Polysaccharide Composition," *Enzyme Microb. Technol.*, vol. 8, No. 10, pp. 588-592 (Oct. 1986) (Abstract).

Ruiz-Herrera, J., "Chemical Components of the Cell Wall of *Aspergillus Species*," *Archives of Biochemistry and Biophysics*, vol. 122, pp. 118-125 (1967).

Sabnis, S. et al., "Improved Infrared Spectroscopic Method for the Analysis of Degree of N-deacetylation of Chitosan," *Polymer Bulletin*, vol. 39, pp. 67-71 (1997).

Sakai, K. et al., "Purification and Hydrolytic Action of a Chitosanase from *Nocardia orientalis*," *Biochimica et Biophysica Acta.*, vol. 1079, pp. 65-72 (1991).

Sannan, T. et al., "Studies on Chitin, 2, Effect of Deacetylation on Solubility," *Makromol. Chem.*, vol. 177. pp. 3589-3600 (1976).

Shahidi, F. et al., "Food Applications of Chitin and Chitosans," *Trends in Food Science & Technology*, vol. 10, pp. 37-51 (1999).

Shu, C-K, "Degradation Products Formed from Glucosamine in Water," *J. Agric. Food Chem.*, vol. 46, pp. 1129-1131 (1998).

Sigma, Biochemicals and Reagents, p. 461 (2000).

Stagg, C. et al., The Characterization of a Chitin-Associated D-Glucan from the Cell Walls of *Aspergillus niger*, vol. 320, pp. 64-72 (1973).

Stainer, R. et al., "The Microbial World," *Prentice-Hall, Inc.*, pp. 332-336 (1970).

Tan, S. et al., "The Degree of Deacetylation of Chitosan: Advocating the First Derivative UV-spectrophotometry Method of Determination," *Talanta*, vol. 45, pp. 713-719 (1998).

Wessels, J. et al., "15 Fungal Cell Walls: A Survey," *Plant Carbohydrates II, Extracellular Carbohydrates*, pp. 352-394 (1981).

Wu, A. et al., "Determination of Molecular-Weight Distribution of Chitosan by High-performance Liquid Chromatography," *Journal of Chromatography*, vol. 128, pp. 87-99 (1976).

Kostina et al., "Chitin of mycelial fungi of the Penicillium genus," Prikl. Biokhim. Mikrobiol. Abstract (1978), 14(4), 586-593.

Novikov, "Kinetics of formation of D-(+)- glucosamine in acid hydrolysis of chitin," Russian Journal Abstract (Sankt-Peterburg) (1999), 72(1), 147-152.

Yang et al., "Acidic hydrolysis and determination of fungal mycelium in cereals," Chinese Journal Abstract, Chinese Agricultural Chimical Society (1998) 36(6), 555-564.

Nilsson et al., "Chitin as an indicator of the biomass of two wood-decay fungi in relation to temperature, incubation time, and media composition," Abstract, Canadian Journal of Microbiology, (1998), vol. 44, No. 6, 575-581.

Plassard et al., "Estimation of mycelial growth of basidiomycetes by means of chitin determination," Abstract, Phytochemistry (Oxford) (1982), vol. 21, No. 2, 345-349.

Jeremy Appleton, *Inadequate Screening of Imported Food and Dietary Supplements*, 2 Integrative Medicine, 58-65 (available at www.ifr.bbsrc.ac.uk/protall/infosheet.htm, Feb./Mar. 2003).

Department of Health and Human Services, *FDA Increases Sampling of Imported Shrimp and Crayfish*, FDA News (2002) (available at www.fda.gov.bbs.topics/NEWS/2002/NEW00815.html, last visited Oct. 18, 2002).

Federal Trade Commission, *Shark Cartilage Receives 10M Draft Monograph*, FTC Notice (2002) (available at www.ftc.gov/opa/2002/09/fdacomments.htm, as of Sep. 2002).

International Search Report and Written Opinion for PCT/US2007/007365, filed Mar. 22, 2007 (Mailed Oct. 22, 2007).

International Search Report and Written Opinion for PCT/US2007/007258, filed Mar. 22, 2007 (Mailed Aug. 29, 2007).

Matsubara, Machiko et al., "Physiological and Biochemical Studies on Germinating Fungal Spores. VII. Chemical Composition of Cell Walls in Conidia of *Cochliobolus miyabeanus*," *Chem. Pharm. Bull.*, vol. 33, No. 3, pp. 1175-1180 (1985).

White, Stephen A. et al., "Production and Isolation of Chitosan from *Mucor rouxii*," *Applied and Environmental Microbiology*, vol. 38, No. 2, pp. 323-328 (Aug. 1979).

Office action dated Mar. 29, 2006 for U.S. Appl. No. 10/382,251, filed Mar. 5, 2003.

English Translation of JP2000281696, published Oct. 10, 2000.

* cited by examiner

US 7,816,514 B2

GLUCOSAMINE AND METHOD OF MAKING GLUCOSAMINE FROM MICROBIAL BIOMASS

CROSS REFERENCE TO RELATED APPLICATIONS

The present application is a continuation-in-part of U.S. patent application Ser. No. 10/326,549 filed Dec. 19, 2002, now U.S. Pat. No. 7,049,433, which is a continuation of U.S. patent application Ser. No. 09/785,695 filed Feb. 16, 2001, now abandoned and claims priority from PCT Application No. PCT/US02/04468 filed Feb. 15, 2002, each of which is incorporated herein by reference.

FIELD

The present invention is directed to glucosamine compositions and to methods of making glucosamine compositions.

BACKGROUND

Glucosamine is a nutraceutical supplement that has been shown to provide significant therapeutic relief for arthritis and joint pain. Although the mechanism is not entirely known, it is believed that glucosamine functions to aid in restoration of the cartilage to relieve inflammation in the joints, thereby providing significant benefit to patients.

Presently, glucosamine is primarily derived from harvested natural sources, such as shellfish and other aquatic organisms. Components of the shell or exoskeleton of these organisms are converted into glucosamine using various production techniques. These natural sources are acceptable for producing glucosamine for some applications, but they have limitations. These limitations include the fact that wild shellfish can have significant variations in their composition because they grow naturally under uncontrolled circumstances. The shellfish can vary in such aspects as their size and composition depending upon the growing conditions as well as their species. Also, without control over the growing conditions, the shellfish can be exposed to environmental contaminants, including heavy metals, that can be retained in glucosamine or other products produced from the shellfish. Shellfish harvests are often seasonal, and thus the supply and price of shellfish shows significant variation over time.

A further concern with glucosamine derived from shellfish is that significant portions of the human population have shellfish allergies and are unable to use products that contain ingredients derived from shellfish. A large percentage of shellfish allergens are specific proteins. Shellfish allergens, such as muscle proteins (e.g., tropomyosin) are found in glucosamine derived from the shellfish sources. It is not economically practical, if even possible to ensure that glucosamine products derived from shellfish sources are completely free of all traces of shellfish allergens. Thus, hyper allergenic individuals who must avoid all shellfish products cannot ingest materials derived from shellfish, such as glucosamine.

An additional problem associated with existing sources of shellfish-derived glucosamine is that some of the shellfish supply is harvested from the seas and oceans of the world. Excessive harvest of shellfish could have a great negative environmental impact. Thus, it is believed that some consumers would prefer to use glucosamine that is not harvested at the expense of sea life. Even if the environmental impact of harvesting shellfish is not negative, there remains concern that the supply of wild shellfish is limited in quantity and inconsistent in quantity from year to year.

Another problem associated with glucosamine compositions derived from shellfish is that such compositions are not "kosher." "Kosher" means fit or proper, and is generally used to describe foods that are prepared in accordance with special Jewish dietary laws. Many people that practice Judaism will only ingest kosher products. All shellfish are non-kosher foods and thus all products derived from shellfish are not considered kosher. Although for certain medicinal applications, a shellfish glucosamine product can receive special dispensation such that it is considered kosher, specially dispensed kosher shellfish-derived glucosamine may be used for medicinal applications only and even then may only be ingested in pill or tablet form. Accordingly, a "fully certified kosher" glucosamine composition (i.e., a kosher product not requiring special dispensation or restricted to medicinal uses in pill or tablet form) is needed. Likewise, many vegans require an animal-product free glucosamine composition and glucosamine compositions derived from shellfish do not meet their dietary needs.

Therefore, a need exists for a source of safe, kosher, non-animal product derived, high-quality glucosamine compositions that can be created economically and with a minimum of environmental impact.

SUMMARY

Disclosed are glucosamine compositions, including glucosamine composition products suitable for human or animal consumption. The disclosed glucosamine compositions are derived from fungal biomass containing chitin. Suitable starting materials include microbial fungal sources, such as fungal sources derived from *Aspergillus* sp., *Penicillium* sp., *Mucor* sp., and combinations thereof. Use of a fungal biomass results in high quality glucosamine compositions that are generally uniform with low levels of impurities. The glucosamine compositions normally have relatively low ash content, and are free of or substantially free of heavy metal contaminants. In addition, as a product of fungal biomass, the glucosamine compositions do not pose a hazard to persons who have shellfish allergies. That is, tropomyosin and other such muscle-derived proteins are not present in fungal biomass. Because the disclosed glucosamine compositions are not derived from shellfish (or any animal source), the disclosed compositions are both kosher and may be consumed by strict vegetarians. Shellfish and products derived from shellfish are not considered kosher by any guidelines regarding kosher products.

Particular embodiments of the disclosed glucosamine compositions comprise glucosamine and no shellfish allergens. Other embodiments of the disclosed glucosamine compositions include kosher glucosamine. Other embodiments of the disclosed glucosamine compositions comprise glucosamine and an absence of animal-derived products. Yet other embodiments of the disclosed glucosamine compositions comprise glucosamine and melanoidins. Further embodiments of the disclosed glucosamine compositions comprise glucosamine, melanoidins, and/or levulinic acid. Other embodiments of the disclosed glucosamine compositions have lipophilic oxygen radical absorbance capacity (ORAC) values of from 30 µmole TE/g to 150 µmole TE/g or from 35 µmole TE/g to 100 µmole TE/g or from 35 µmole TE/g to 50 µmole TE/g.

Also disclosed are various methods for producing glucosamine compositions by acid hydrolysis of fungal biomass. The methods for obtaining glucosamine compositions from microbial biomass include, for example, reacting chitin-containing biomass in a relatively concentrated acidic solution at a relatively elevated temperature. Also disclosed are methods for obtaining glucosamine compositions from microbial biomass by, for example, reacting the chitin-containing biomass in a relatively mild acidic solution and then in a relatively concentrated acidic solution. In an alternative embodiment, the microbial chitin-containing biomass is reacted with a basic solution before or after acid hydrolysis treatment. In yet another embodiment, fungal biomass is treated with an acidic solution at an elevated temperature and/or pressure to produce glucosamine compositions.

DRAWINGS

DETAILED DESCRIPTION

Figure 1:
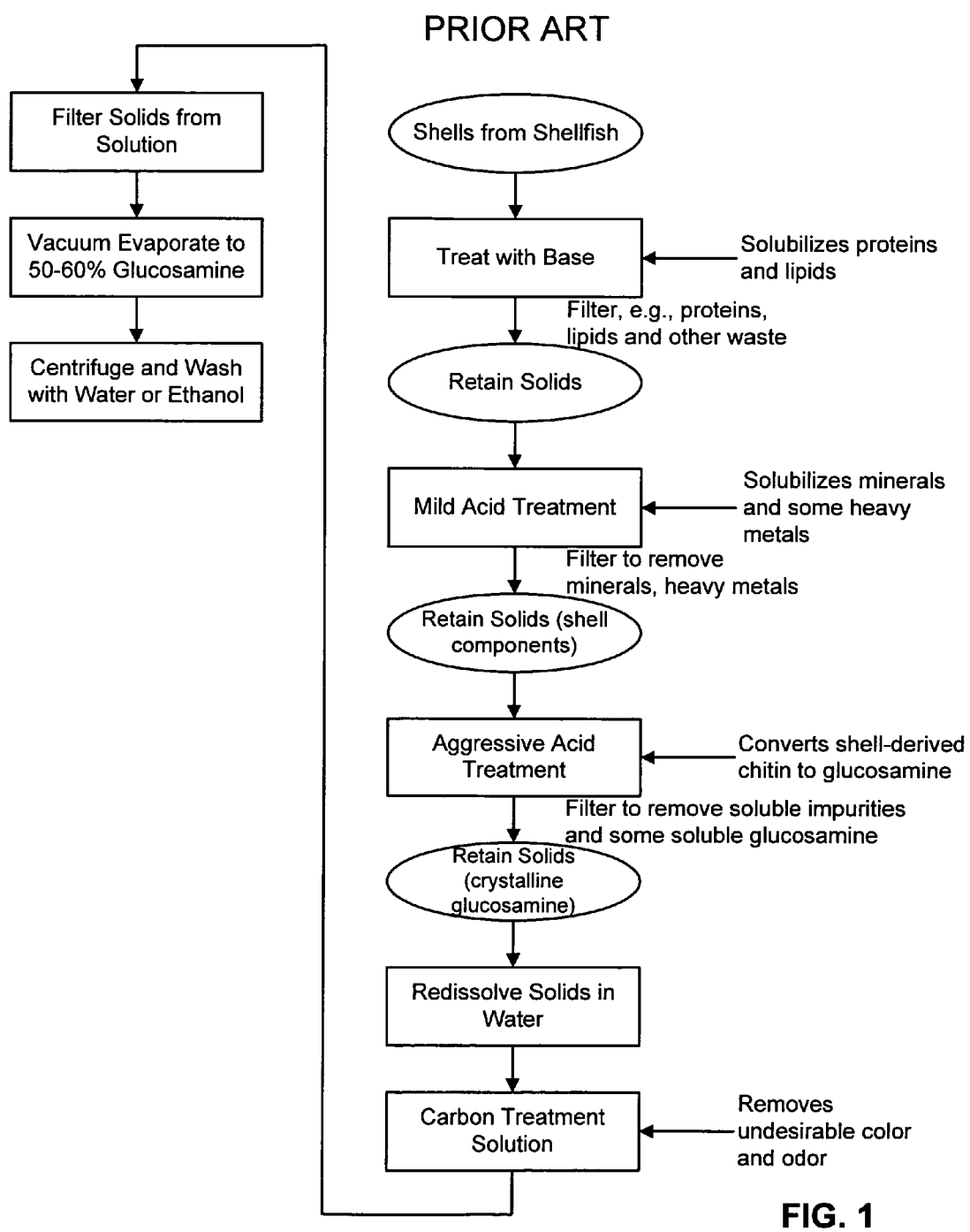
FIG. 1 is a prior art flow diagram illustrating a process for producing glucosamine from shellfish.

Disclosed are glucosamine compositions and glucosamine composition products, such as food supplements, suitable for human or animal consumption. The glucosamine compositions are derived from chitin present in various types of fungal biomass. Chitin is a natural polysaccharide, with the structure of an unbranched polymer of 2-acetoamido-2-deoxy-D-glucose (N-acetyl-D-glucosamine). The formula for chitin can be represented by the general repeating structure:

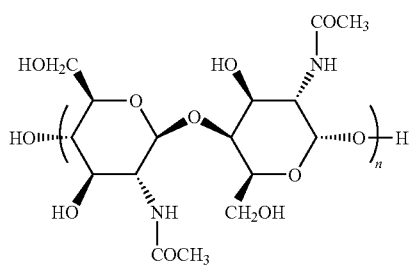

Chitin is typically an amorphous solid that is largely insoluble in water, dilute acids, and alkali. Although chitin has various commercial applications, commercial utility can be found by transforming the polymeric structure into individual components of 2-amino-2-deoxy-D-glucose, which is known as glucosamine. Structurally, glucosamine is modified glucose with an amine group replacing the OH group found on the carbon two (C-2) atom. The general structure of glucosamine is:

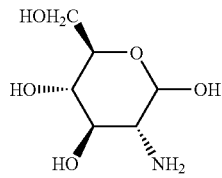

As stated above, glucosamine compositions disclosed herein include glucosamine derived from fungal biomass containing chitin and may include other components as well. Suitable starting materials for producing the glucosamine compositions include substantially uniform microbial fungal sources, such as fungal sources derived from Aspergillus sp., Penicillium sp., Mucor sp. and combinations thereof. Use of a fungal biomass results in a high-quality product that produces glucosamine compositions having low levels of impurities, such as undesirable minerals. The glucosamine compositions normally have relatively low ash content and thus, no or at most trace levels of heavy metals. In addition, low ash content provides relatively clear solutions made from the glucosamine compositions.

In addition, because the glucosamine compositions are products of fungal biomass, the glucosamine compositions disclosed herein are not subject to inclusion of the protein allergens found in glucosamine produced from shellfish.

A. Glucosamine Compositions

The glucosamine compositions may be derived from relatively uniform fungal biomass sources, so that the glucosamine compositions are generally uniform. "Uniform fungal biomass" refers to fungal biomass comprising substantially the same species grown on substantially the same media, grown in a relatively controlled environment or other such conditions that lead to substantial uniformity in the biochemical make-up of the biomass. Depending upon the methodology used to purify the glucosamine compositions such as desired glucosamine salt compositions, the resulting glucosamine containing compositions can be produced with varying amounts of glucosamine, including compositions that exceed 95 percent glucosamine, 98 percent glucosamine, and even 99.8 percent glucosamine. The glucosamine compositions can contain additional ingredients, such as salts, melanoidins and acids, e.g., levulinic acid (as discussed below). Certain of the glucosamine compositions include 0.01 to 10% glucose, 0.01 to 5% glucose, or 0.01 to 2% glucose.

Unless otherwise indicated, all numbers expressing quantities of ingredients, properties such as molecular weight, percentages, reaction conditions, and so forth used in the specification and claims are to be understood as being modified by the term "about." Accordingly, unless indicated to the contrary, the numerical parameters set forth are approximations that may depend upon the desired properties sought.

The glucosamine in the disclosed compositions has the general formula represented below:

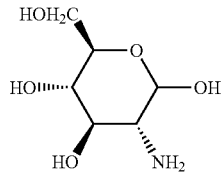

This general formula varies in different embodiments of the glucosamine compositions depending upon the presence of various salts of the glucosamine, including citrate, acetate, phosphate, sulfate, chloride, lactate, gluconate, etc. Also, the glucosamine in the glucosamine compositions can be substituted or modified without diverging from the scope of the invention. Thus, as used herein, the term glucosamine refers to the various forms of glucosamine, including salt complexes and substituted glucosamine. Likewise, the term glucosamine composition refers to compositions including glucosamine in such various forms.

Embodiments of the glucosamine compositions include particular components in addition to glucosamine, such as glucose, unreacted chitin, and glucan conversion materials, such as melanoidins and levulinic acid.

Melanoidins are relatively complex, high molecular weight, irregular polymers and are present in particular embodiments of the glucosamine compositions. For example, particular embodiments of the disclosed glucosamine compositions include from 0.001 to 15 wt. % melanoidins, or from 0.001 to 1.0 wt. % melanoidins or from 0.01 to 0.1 wt. % melanoidins. Without being tied to any particular theory, melanoidins are likely formed by the conversion of glucans to dextrose to hydroxymethylurfural (HMF) to produce the melanoidins. (The reaction may produce other glucan-derived products and amines from proteins in a biomass source as well as lipids in such a source.) Such a chemical process is known as the Maillard Reaction.

Levulinic acid (also known as acetyl-propionic acid) is present in particular embodiments of the disclosed glucosamine compositions. Without being tied to any particular theory, levulinic acid is likely formed when glucans in the fungal biomass are converted to dextrose, which is converted to HMF to finally form formic and levulinic acids. Levulinic acid is a non-hazardous component that is a valuable acidulant used in such products as carbonated and fruit juice beverages, jams, and jellies. Thus, addition of embodiments of the glucosamine compositions to such products provides an acidulant benefit as well as the benefits provided by the glucosamine in the composition. Particular embodiments of the glucosamine compositions include from 0.0001 to 1 wt. % levulinic acid, or from 0.001 to 0.7 wt. % levulinic acid or from 0.01 to 0.4 wt. % levulinic acid.

Because the melanoidins and levulinic acid are formed when producing the glucosamine compositions according to the disclosed methods, no additional steps must be taken to include such components in the compositions. Melanoidins and levulinic acid were not expected in glucosamine compositions derived from shellfish, and analysis of six lots of glucosamine derived from shellfish (obtained from five different suppliers) did not contain any detectable amounts of melanoidins or levulinic acid.

Figure 7:
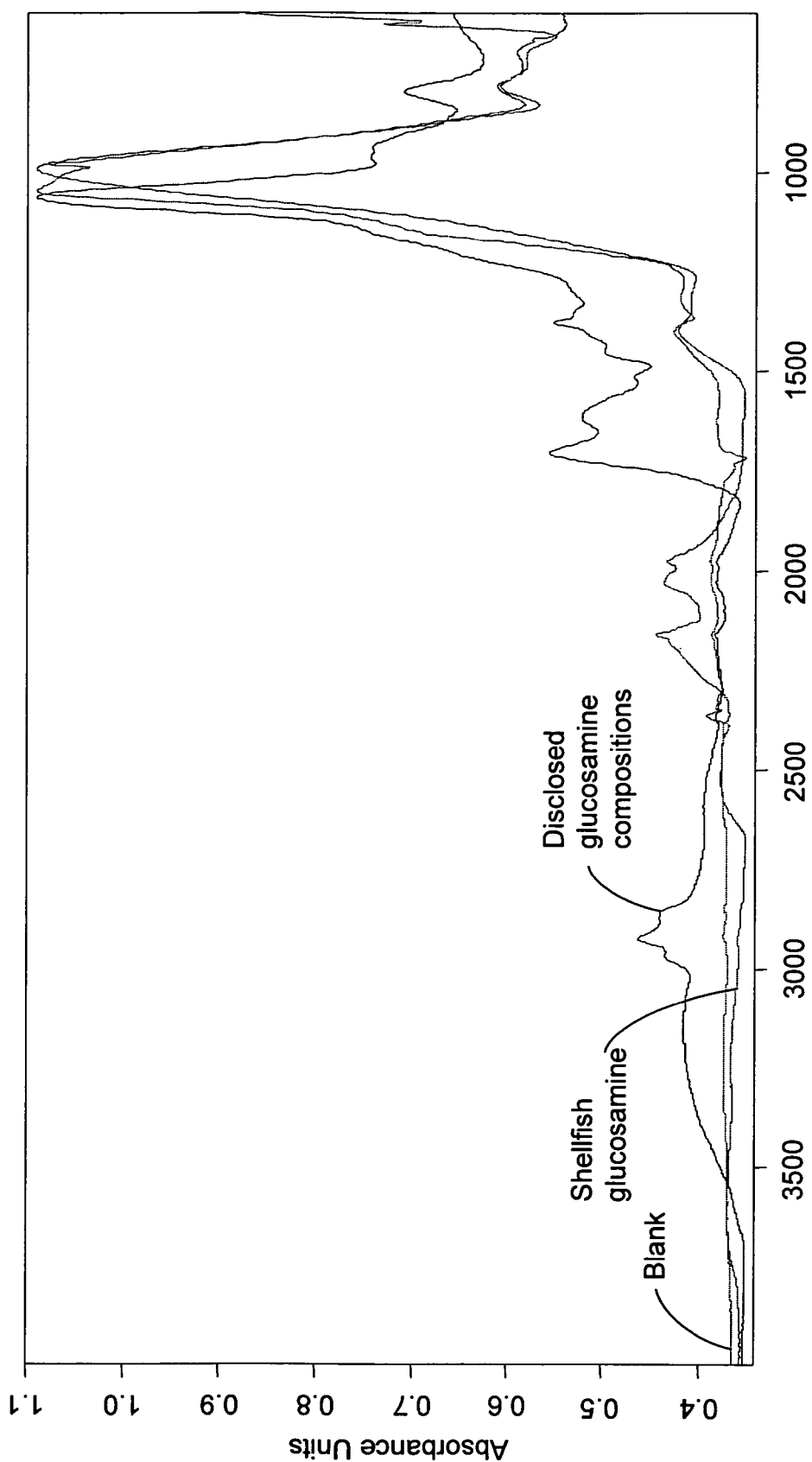
FIG. 7 is an FTIR spectra showing comparison of certain of the presently disclosed glucosamine compositions to glucosamine materials derived from shellfish.

As discussed, complex carbohydrates in fungal biomass, such as glucans, are converted to melanoidins in the reducing environment of the process. These complex carbohydrates are not present in the shellfish carapaces used in other processes, and so the melanoidins do not form. Comparison of FTIR spectra (FIG. 7) of water-insoluble materials in certain embodiments of the disclosed glucosamine compositions to those found in a typical shellfish-derived glucosamine shows that melanoidins are not present in shellfish derived glucosamine compositions. The FTIR spectrum of the insoluble material from the disclosed glucosamine composition has several broad bands with no fine structure, typical of polymeric materials. The bands between 2800 and 3000 wave numbers in the spectrum of the present compositions are typical of amide groups in melanoidins. The insoluble material from the shellfish derived glucosamine product has no such indications of the presence of melanoidins in the FTIR spectra.

Because melanoidins are irregular polymers with reduced carbon, some degree of conjugation exists between the pi bonds. This conjugation results in the typical tan to brown color of melanoidins. Such coloration was clearly present in embodiments of the presently disclosed glucosamine compositions but was absent in the shellfish-derived glucosamine samples again indicating that shellfish derived glucosamine compositions do not include melanoidins.

Melanoidins are reported to possess antioxidant and/or free radical scavenging character. See, e.g., Gow-Chin Yen, et al., *Antioxidant Activity and Scavenging Effects on Active Oxygen of Xylose-Lysine Maillard Reaction Products*, J. Sci. Food Agric., 67, 415-420 (1995); K. Eichner, *Antioxidant Effect of Maillard Reaction Intermediates*, Prog. Fd. Nutr. Sci., 5, 441-451 (1981); Fumitaka Hayase, et al., *Scavenging of Active Oxygens by Melanoidins*, Agric. Biol. Chem, 53(12), 3383-3385 (1989); Dejian Huang, et al., *High-Throughput Assay of Oxygen Radical Absorbance Capacity (ORAC) Using a Multichannel Handling System Coupled with a Microplate Fluorescence Reader in 96-Well Format*, J. Agric. Food Chem., 50, No. 16, 4437-4444 (2002), each of which is incorporated herein by reference. Certain embodiments of the glucosamine compositions disclosed have lipophilic oxygen radical absorbance capacity values (lipo-ORAC values) of from 30 µmole TE/g (TROLOX equivalent per gram) to 150 µmole TE/g or lipo-ORAC values of from 35 µmole TE/g to 100 µmole TE/g or from 35 µmole TE/g to 50 µmole TE/g. TROLOX is also known as 6-hydroxy-2,5,7,8-tetramethyl-2-carboxylic acid.

The lipo-ORAC values may be determined, e.g., by use of an ORAC assay using fluorescein (FL) as a fluorescent probe as discussed in Dejian Huang, et al., *Development and Validation of Oxygen Radical Absorbance Capacity Assay for Lipophilic Antioxidants Using Randomly Methylated β-Cyclodextrin as the Solubility Enhancer*, J. Agric. Food Chem., 50, No. 7 (2002), which is incorporated herein by reference. Randomly methylated β-cyclodextrin (RMCD) is used as a water solubility enhancer for lipophilic antioxidants. Seven percent RMCD (w/v) in a 50% acetone-water mixture is used to solubilize the lipophilic antioxidants in 75 mM phosphate buffer (pH 7.4). When using TROLOX as the standard (1.0), α-tocopherol, (+)-γ-tocopherol, (+)-δ-tocopherol, α-tocopherol acetate, tocotrienols, 2,6-di-tert-butyl-4-methylphenol, and γ-oryzanol have ORAC values of 0.5+/−0.02, 0.74+/−0.03, 1.36+/−0.14, 0.00, 0.91+/−0.04, 0.16+/−0.01, and 3.00+/−0.26, respectively, when using this method.

Levulinic acid and dextrose, present in certain embodiments of the disclosed glucosamine compositions are not expected to be present in glucosamine derived from shellfish. High performance liquid chromatography demonstrates the differences between embodiments of the glucosamine composition disclosed herein and shellfish-derived glucosamine compositions. Neither levulinic acid nor dextrose was detected in any shellfish-derived glucosamine products.

Figure 8:
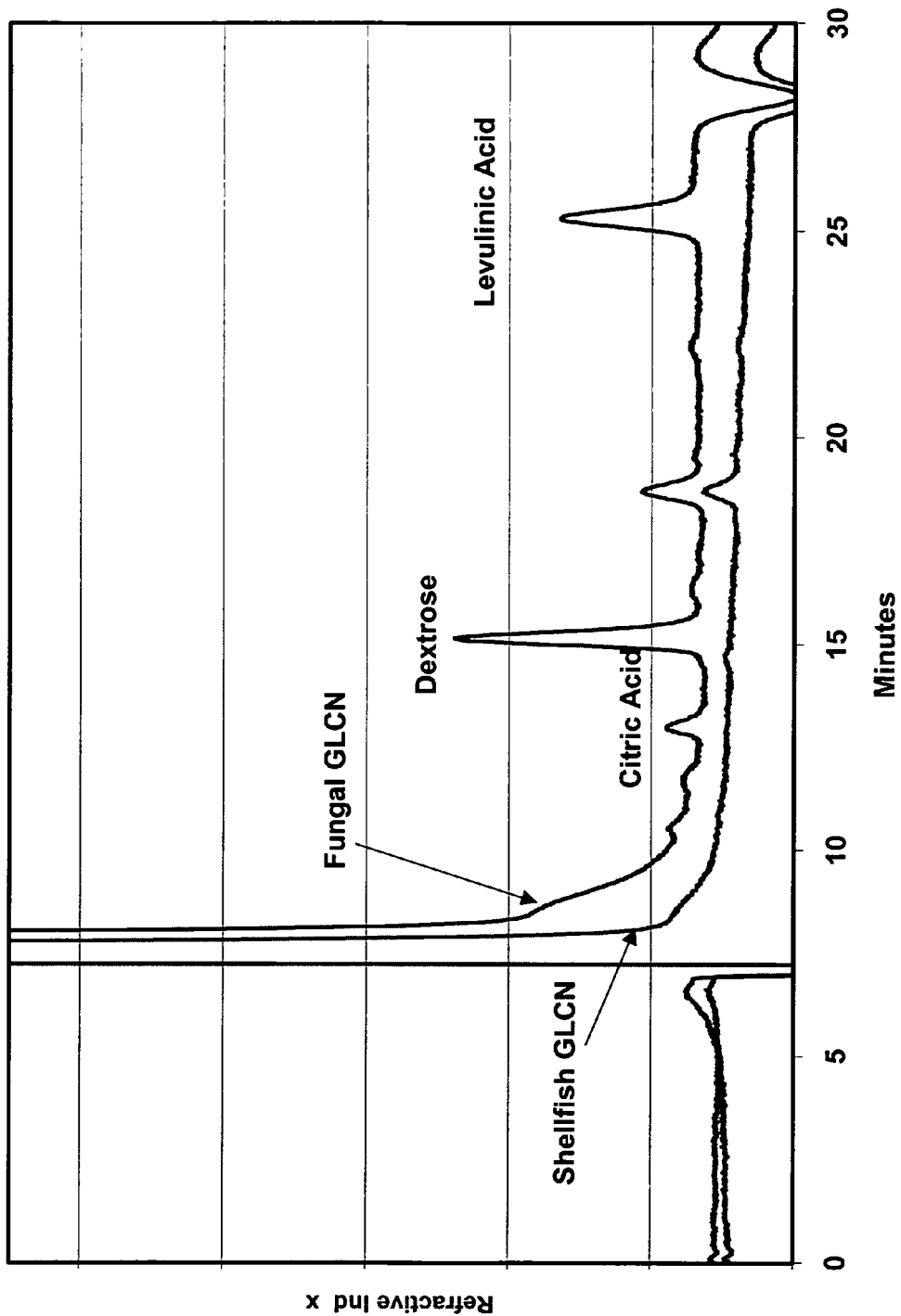
FIG. 8 is an HPLC chromatogram that compares water-soluble components of an embodiment of the disclosed composition to glucosamine derived from fungal biomass indicating that no levulinic acid or dextrose was detected in the shellfish-derived glucosamine.

Specifically, samples of the present compositions and shellfish-derived glucosamine compositions were dissolved in 0.01 N sulfuric acid at a concentration of 4% w/v. Diluted samples were filtered through 0.2 mm nylon filters into HPLC vials. Chromatograms were collected using a Metacarb H Plus column (Varian, Inc., Torrence, Calif.) using 0.01 N sulfuric acid as the eluent at 0.4 mL/min. Peaks were identified by retention time against known standards. As is apparent in FIG. 8, levulinic acid and dextrose were present only in the presently disclosed glucosamine compositions and not in the shellfish derived compositions.

With reference to Table 1, embodiments of the glucosamine compositions comprise glucosamine derived from fungal biomass and may also comprise one or more of the listed components in Table 1, those shown in Table 2 and other components as discussed herein. Concentrations of each component may be within the ranges shown or may be varied by altering any of a variety of production parameters.

TABLE 1

| Glucosamine Composition Components | Representative Embodiment Percent by Weight | Representative Embodiment Percent by Weight | Representative Embodiment Percent by Weight |
|---|---|---|---|
| Glucosamine | 85-99.8 | 95-99.8 | 98-99.8 |
| Melanoidins | 0.001-15 | 0.001-1.0 | 0.01-0.1 |
| Levulinic Acid | 0.0001-1 | 0.001-0.7 | 0.01-0.4 |
| Dextrose | 0.001-10 | 0.001-5 | 0.001-2 |
| Citric Acid | 0.001-10 | 0.01-1.0 | 0.025-0.5 |

With reference to Table 2, two specific embodiments of the glucosamine compositions are set forth. The methods utilized to determine the components present and concentrations of the same are set forth below.

TABLE 2

| Composition Component | *Embodiment 1 (GP-11) | *Embodiment 2 (GP-17C) |
|---|---|---|
| Ash Content | 0.03% | 0.02% |
| Si | 140 ppm | 150 ppm |
| Na | 10-100 ppm | 10-100 ppm |
| K | 10-100 ppm | 10-100 ppm |
| Ca | 10-100 ppm | 10-100 ppm |
| HCL | 0.16% | 0.19% |
| Citric Acid | 0.045% | 0.074% |
| Levulinic Acid | 0.39% | 0.3% |
| Melanoidins | 0.04-0.07% | 0.02-0.03% |
| Water-insoluble matter soluble in gastric juice at ~40° | 0.05% | 0.02% |

*Percentages listed are percents by weight

Certain embodiments of the glucosamine compositions have relatively low ash content. The ash content may be less than 5 percent, less than 2 percent, or less than 1 percent. There are little if any heavy metal components in the glucosamine compositions; the heavy metal component concentrations in the disclosed glucosamine compositions are well below 100 parts per million, more typically below 50 parts per million, even more typically below 20 parts per million. In certain embodiments the heavy metal components are present in less than 10 parts per million.

The glucosamine component of the glucosamine compositions can have a positive specific rotation, such as a positive 69 to 74 degree specific rotation for the glucosamine hydrochloride salt. The glucosamine compositions are usually relatively white when in purified dry form, but colorless when dissolved in an aqueous solution. In one example, a 20 percent by weight solution of the glucosamine has an American Public Health Association (APHA) color of less than 50.

The glucosamine compositions may also be combined with further components to form a food supplement for human and/or animal ingestion. For example, the glucosamine compositions may be further combined with excipient, common pharmaceutical binders (e.g., sucrose, glucose, ethyl cellulose, methyl cellulose, polyvinyl pyrrolidone, polyethylene glycol, lactose, dicalcium phosphate, crospovidone, croscarmellose, and the like), common organic acids (e.g., citric acid, malic acid, tartaric acid, lactic acid, and the like), and/or carbohydrates (e.g., starch, glucose, sucrose, and the like). Such glucosamine compositions may also be combined with sugars, artificial sweeteners, natural and artificial colors, natural and artificial flavorings, acidulants, thickeners, and the like, to form a variety of food supplements. Such glucosamine composition food supplements are typically made into food supplement beverages, bars, concentrates, dry or concentrated drink mixes, powders, chews, confections, gums, yogurts, patches, lozenges, and the like.

B. Microbial Fungal Biomass Starting Materials

Suitable starting materials for producing the disclosed glucosamine compositions include microbial biomass sources, typically fungal biomass, such as filamentous fungi having greater than 10 percent chitin by total dry cell weight, such as fungal sources derived from *Aspergillus* sp., *Penicillium* sp., *Mucor* sp. Suitable fungal biomasses include *Aspergillus niger, Aspergillus terreus, Aspergillus oryzae, Mucor rouxii, Penicillium chrysogenum, Penicillium notatum, Saccharomyces cerevisiae; Saccharomyces uvarum*; and in particular *Candida guillermondi, Aspergillus niger*, and *Aspergillus terreus*. The biomass may be recovered from a commercial fermentation reaction, such as the commercial production of organic acids, including citric acid. Also, biomass suitable for production of glucosamine can be generated specifically for this process and not as a byproduct of other processes. As used herein, the term microbial does not include phyto-plankton and crustaceans or mollusks.

Biomasses having chitin levels in excess of 5 percent of the dry biomass weight are suitable for practicing the methods disclosed. Such biomass usually has between 5 and 25 percent chitin, and can have from 10 to 20 percent chitin, based upon dry weight of the biomass. Also, in order to prepare food or supplemental grade glucosamine compositions it is sometimes desirable that the microbial biomass be grown in a substantially controlled manner having relatively uniform temperature and/or nutrient levels during the growth of the biomass. Nutrient levels can be controlled by any suitable manner, for example as disclosed in U.S. Pat. Nos. 2,739,923, 2,353,771, and 2,674,561, which are incorporated herein by reference.

C. Methods for Producing Fungal Biomass Glucosamine Compositions

Also disclosed are methods for producing glucosamine compositions from fungal biomass sources, including producing such compositions by acid hydrolysis of fungal biomass. Acid hydrolysis breaks ether linkages in the biomass and deacetylates chitin molecules to generate free glucosamine. Acid hydrolysis can break the chitin into glucosamine, but leaves the glucosamine molecule substantially intact. Depending upon the acid hydrolysis parameters, acid hydrolysis conditions break down other components (such as glucans, proteins, and lipids) that exist in the fungal biomass.

In one specific of the disclosed method for producing glucosamine compositions from fungal biomass, acid hydrolysis is performed by treating fungal biomass for a relatively long period of time, for example greater than 4 hours, in a relatively aggressive acid solution.

Figure 2:
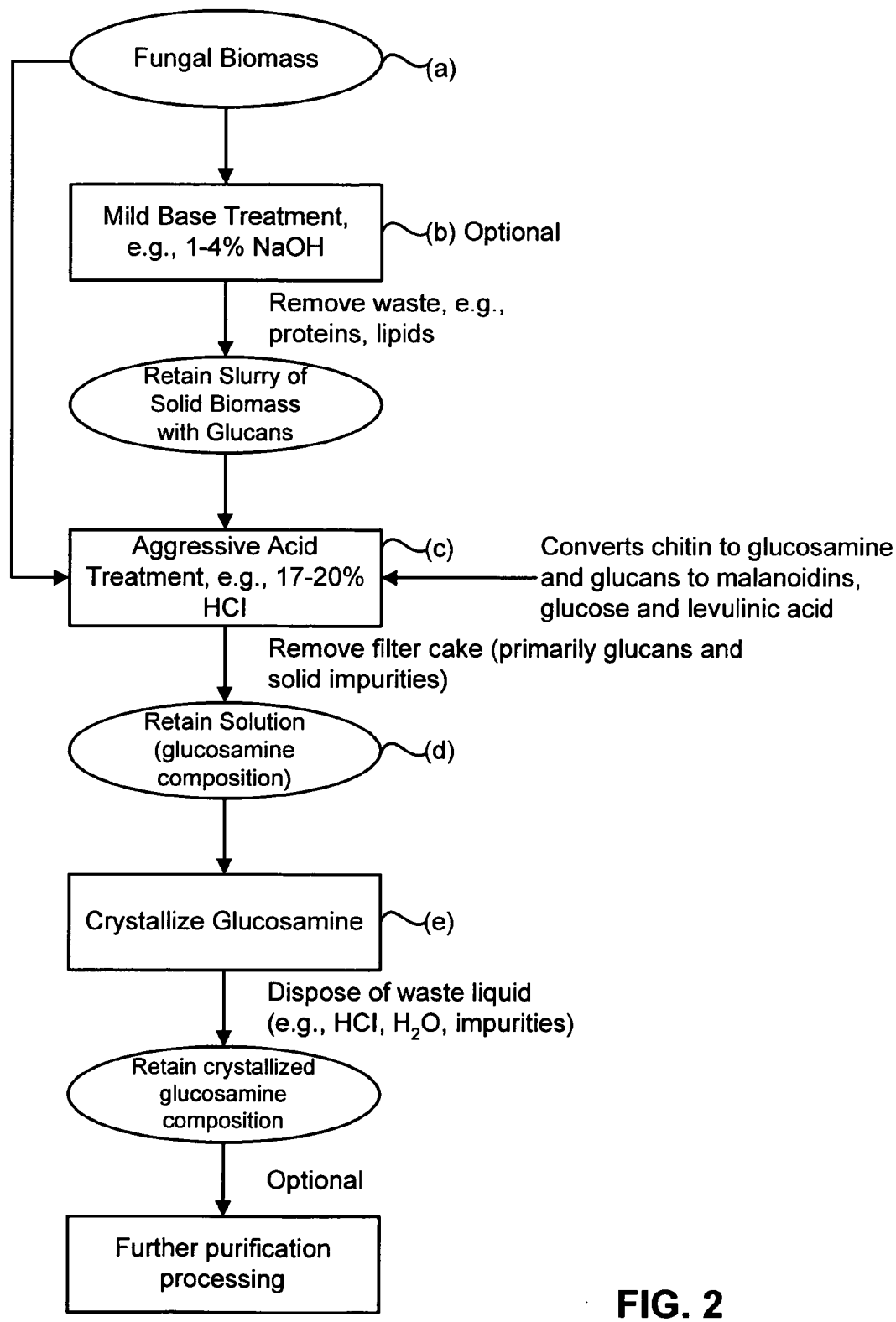
FIG. 2 is a flow diagram of one of the disclosed methods for producing particular embodiments of the glucosamine compositions.

With reference to FIG. 2, chitin-containing fungal biomass (a) may first be reacted in a relatively aggressive acidic solution (c). Relatively strong (aggressive) acids may be used to hydrolyze the fungal biomass, including acids of concentrations less than 50 percent. Acids of concentrations of from 5 to 25 percent are also suitable. Suitable strong acids include hydrochloric, sulfuric, phosphoric, and citric acid at appropriate concentrations.

In particular embodiments of the disclosed methods particular glucosamine compositions are formed by an aggressive acid treatment, reacting from 5 to 20 percent acid with from 2 to 50 percent pretreated biomass (based upon dry weight, although the biomass is typically processed with water present) and from 35 to 93 percent water. In certain implementations the reaction mixture comprises from 8 to 12 percent hydrochloric acid, from 4 to 8 percent biomass (based upon dry weight), and from 80 to 90 percent water. In yet another embodiment, the acid solution is from 17 to 20 percent hydrochloric acid solution.

The aggressive acid treatment mixture containing the biomass, acid, and water is heated and maintained at a relatively elevated temperature. The mixture is usually heated to a temperature at or near its boiling point (typically 90° C. to 106° C.) and maintained under reflux conditions for 5 hours or greater, more typically greater than 8 hours, and usually less than 16 hours. The reaction may continue long enough to have a complete breakdown of the chitin, but not so long as to be inefficient or to excessively decompose the glucosamine compositions.

Although reaction in the relatively aggressive acid solution produces a glucosamine composition, subsequent purification steps may be taken. A first purification step may include a separation step, such as filtration, to remove particulate impurities, resulting in a substantially clear solution of the glucosamine composition, (d) in FIG. 2. The solution contains an embodiment of glucosamine composition as well as small quantities of glucose and other components of the composition. The glucosamine composition can be concentrated and some of the acid recovered can be recycled and reused.

The glucosamine composition may be crystallized, (e) in FIG. 2. For example, the glucosamine composition may be crystallized by adding ethanol to the concentrated solution or by continuing evaporation to the glucosamine composition solubility limit.

The glucosamine composition can be recovered by a separation process, such as filtration or centrifugation, followed by drying. The dried glucosamine composition is optionally further treated to remove undesirable residual sugars. One method of removing such sugars is by dissolving the glucosamine composition in water and adding ethanol to again precipitate the glucosamine composition while undesirable sugars remain in solution. Alternatively, the solution can be treated by electro dialysis, chromatography, membrane filtration, or other suitable procedures to further increase the concentration of glucosamine in the glucosamine composition. The glucosamine composition may optionally be decolorized and/or deodorized by, for example, treating the composition with ethanol, carbon, or other suitable material or method.

Such an aggressive acid hydrolysis method typically has a yield of glucosamine composition of greater than 50 percent of the total chitin content of the fungal biomass starting material.

In an alternative embodiment of the method set forth above, the biomass can initially be treated to remove some impurities and/or to improve glucosamine composition production. These treatments can include, for example, heating the biomass, adding digestive enzymes, mixing with an acid or base, mechanical agitation, or dewatering by compression. One optional treatment for removing proteins, lipids, and residual citric acid involves pretreating the biomass in the presence of a base, such as sodium hydroxide ((b) in FIG. 2).

In certain embodiments a concentration of less than 10 percent sodium hydroxide is added to the fungal biomass. The basic solution is heated to a relatively elevated temperature for a period of time sufficient to remove a desirable amount of the non-chitin containing material, such as proteins and lipids. This period of time may be less than two hours. One specific example of this pretreatment method involves heating the fungal biomass to from 100° to 125° C. in a 1 to 8 percent solution of sodium hydroxide for 20 to 60 minutes. Alternatively, the sodium hydroxide concentration may be 1 to 4 percent. Embodiments wherein the biomass is treated with a basic solution, protein and glucans are hydrolyzed in the biomass. These byproducts may optionally be removed by, for example, filtration. The removal of such proteins and other waste products may be followed by treatment to remove soluble proteins, amino acids, and other impurities.

An alternative to treating the biomass with a basic solution could include, for example, treating the fungal biomass in solution with protease enzymes or other suitable enzymes to remove undesirable components such as proteins and lipids. Yet another alternative embodiment comprises mechanically treating the fungal biomass to physically break down the cell walls so that undesirable proteins and lipids within the cells can be removed prior to extracting the chitin from the cell walls themselves. In yet another alternative embodiment, alcohols are used to remove undesirable components from the fungal biomass prior to acid hydrolysis.

In another embodiment of the method for producing glucosamine compositions from fungal biomass, the biomass material may undergo a mild acid pre-treatment followed by an aggressive acid treatment.

Figure 3:
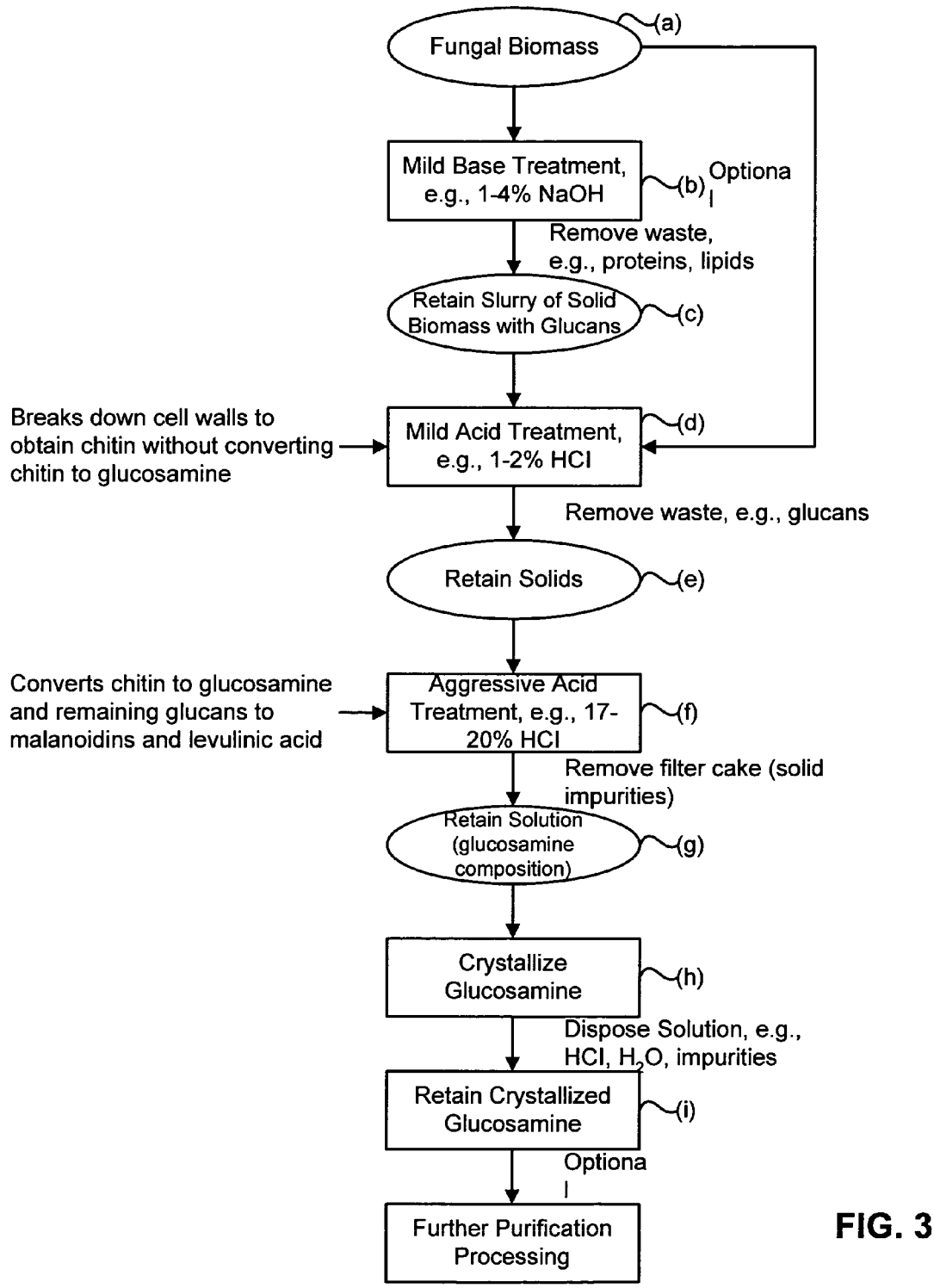
FIG. 3 is a flow diagram of another of the disclosed methods for producing embodiments of the glucosamine compositions.

More specifically, with reference to FIG. 3 chitin-containing biomass (a) may first undergo a mild acid pre-treatment (d). The acid hydrolysis conditions (parameters comprising time, temperature, and acid concentration) used are "mild" in comparison to the subsequent aggressive acid treatment (f). The acid hydrolysis that occurs under the relatively mild conditions allows removal of undesirable constituents from the biomass prior to the aggressive acid treatment (f). A mild acid treatment therefore may be used to improve any one of several aspects of producing the glucosamine composition from fungal biomass. A mild acid can be used to break down the cell walls of the fungal biomass such that extraneous biomass constituents, such as proteins, lipids and undesirable polysaccharides can be removed prior to hydrolyzing the chitin. The acid concentration during mild acid treatment may be from 0.05 to 20% or 0.1 to 12%, or from 0.5 to 5% w/w acid, such as HCl. As with the aggressive acid treatment acid percentage ranges vary depending upon the type of acid used. For example, citric acid will require higher percentage ranges while HCl is suitable at the ranges set forth above. Higher concentrations of strong acid solutions or the use of different acids or mixed acids may be used to break down the cell walls more quickly, yet reaction conditions must be adapted to control the undesirable, premature conversion of the chitin to glucosamine. Likewise lower concentrations of strong acids, weak acids or mixed acids may be used (especially at relatively higher temperatures, for longer time periods, or at higher concentrations) such that the cell walls are sufficiently broken down to afford removal of a substantial or desirable portion of the extraneous biomass constituents, e.g., lipids, proteins and undesirable polysaccharides.

A mild acid treatment (d) may be performed by reacting the following components: from 0.05 to 20 percent acid, and from 1 to 50 percent biomass (based upon dry weight). In certain implementations the mild acid reaction mixture comprises from 0.1 to 12 percent hydrochloric acid, and from 3 to 25 percent biomass (based upon dry weight). In yet another embodiment the solution amounts comprise from 0.5 to 5 percent hydrochloric acid and from 5 to 15 percent biomass (based upon dry weight).

The mild acid treatment may be carried out at a temperature of 60° C. to reflux temperature or from 70° C. to 105° C., or at a temperature of 80° C. to 100° C. Higher temperatures may be used as long as it is not so high as to convert a significant amount of the chitin to glucosamine. Likewise, lower temperatures (such as 60° C.-90° C.) may be used (especially with relatively concentrated acids) as long as the cell walls are sufficiently broken down to release the waste products, e.g., lipids, proteins, and undesirable polysaccharides, without converting a significant amount of chitin to glucosamine. As used herein "a significant amount of chitin to glucosamine" means less than an amount that would provide a low yield of glucosamine in the final glucosamine composition, less than 10% of the chitin, or less than 5% of the chitin, or less than 2% of the chitin.

Prior to or following the mild acid treatment, the fungal biomass (a) (or the solids (e) retained after the mild acid treatment (d) removal of the undesirable products) may optionally be treated with a mildly basic solution (b) as described above and as referenced in FIG. 3. Although method steps are shown and described in specific orders, it is to be understood that the order of these steps may be varied without departing from the disclosed methods.

The solids (e) retained after the mild acid treatment (and optionally the mild base treatment (b)) are then treated with an aggressive acid (f) as discussed in the embodiment above. In this embodiment, however, a large portion of the impurities, primarily glucans, have already been removed from the solution (between steps (d) and (e)). Accordingly, the aggressive acid treatment (f) to convert chitin in the remaining solids from the fungal biomass to a glucosamine composition requires significantly less acid. For example, with an aggressive acid treatment under conditions such as 17% HCl and 10% dry biomass solids for 9 hours at 100° C., the hydrochloric acid needed in the aggressive acid step could be reduced by from 20 to 60%.

When a mild acid treatment and waste product removal process is performed prior to an aggressive acid treatment, because less acid need be used, the amount of final resulting waste solution (between steps (h) and (i)) is a significantly smaller volume as compared to the method omitting the mild acid treatment. The acid needed to treat the biomass is typically extremely expensive; a smaller volume of acid is a significant cost savings, especially when producing the product on a commercial scale. The smaller volume of acidic solution also allows for smaller separation apparatus to separate the glucosamine composition from the acidic solution. Because apparatus needed to separate such a concentrated acid solution must be formed of special (and expensive) materials resistant to the corrosive activities of concentrated acids, smaller separation apparatus saves a significant amount in costs of manufacturing glucosamine compositions from fungal biomass, especially on a commercial scale. When a mild acid treatment precedes the aggressive acid treatment the smaller volume of acidic solution results in less waste solution to be treated once the glucosamine composition is removed therefrom.

Glucosamine compositions are formed during the aggressive acid treatment following a mild acid treatment in the same manner as compositions formed with aggressive acid treatment alone.

When the chitin in the remaining solid (e) is treated with the aggressive acid (f), glucans not removed in the preceding separation process are converted to beneficial glucosamine composition components, such as melanoidins and levulinic acid. To alter the concentrations of such components of the glucosamine composition, one may allow more of the glucans to remain in the remaining solid (e).

Process steps following the aggressive acid treatment (f) are substantially similar to those discussed above.

In yet another embodiment of the methods for producing glucosamine compositions from fungal biomass, increased temperatures and/or pressures are utilized with an aggressive acid treatment. This allows the reaction to occur using less acid or in a shorter time period than the above-mentioned aggressive acid treatment. Temperature ranges for this the increased temperature, aggressive acid treatment are from 90° C. to 160° C., for example, from 105° C. to 160° C. The pressure may be allowed to build as a function of reactions taking place in a sealed vessel.

More specifically, fungal biomass is treated at the aggressive acid treatment phase with an acid, such as from 4 to 20% acid or from 6 to 13%. The lower concentrations of acid still convert the chitin in solution to glucosamine because the reaction conditions are changed to increase the temperature and/or the pressure parameters. Specifically, the acid/biomass solution is placed in a sealed vessel such that the reaction may take place at pressures of slightly over atmospheric to 10 atmospheres, or slightly over atmospheric to 4 atmospheres, such as at 2 atmospheres. The increased pressures may be due to the reaction taking place at an increased temperature in a sealed vessel or the reaction may take place in a vessel in which the pressure is otherwise made to increase.

The temperature, if elevated, is preferably from 90° C. to 160° C., or 100° C. to 140° C., such as 110° C. to 130° C. The reaction may take place at such elevated temperatures at the pressures set forth above or outside a closed vessel at atmospheric pressure. If the temperature of the reaction takes place at from 90° C. to 160° C. in a closed vessel, the pressures will generally be at atmospheric pressure to 5 atmospheres (65 psig). Good results are obtained with, e.g., a reaction temperature of 120° C. and a pressure of 1 atmosphere (or 15 psig).

Other methods of increasing the temperature are available and included in the methods proposed, for example, increasing the boiling point by adding salts.

The remainder of the increased temperature and/or pressure methods for producing glucosamine compositions from fungal biomass follows those steps outlined in the above-described methods (such as shown in FIG. 2 or 3). Specific examples of the increased temperature and/or pressure methods for producing glucosamine compositions are set forth below.

D. EXAMPLES

The invention will be further explained by the following non-limiting illustrative examples. Unless otherwise indicated, all amounts are expressed in parts by weight.

Example 1

Citric biomass was pretreated with a 4 percent aqueous sodium hydroxide (NaOH) solution in an autoclave at 120° C. for 1 hour. This step removed excess proteins and other undesirable materials. The biomass was then thoroughly washed with de-ionized water until its pH was approximately 7.0. This washed material was mixed with concentrated hydrochloric acid (HCl) and water to form a mixture of 10 to 15 percent HCl and 5 to 6 percent biomass, based upon dry weight of the biomass. This mixture was heated at reflux. Samples were taken from time to time, and the reaction analyzed with a high-pressure liquid chromatograph available from Dionex HPLC under the trade designation "DX-500".

Figure 4:
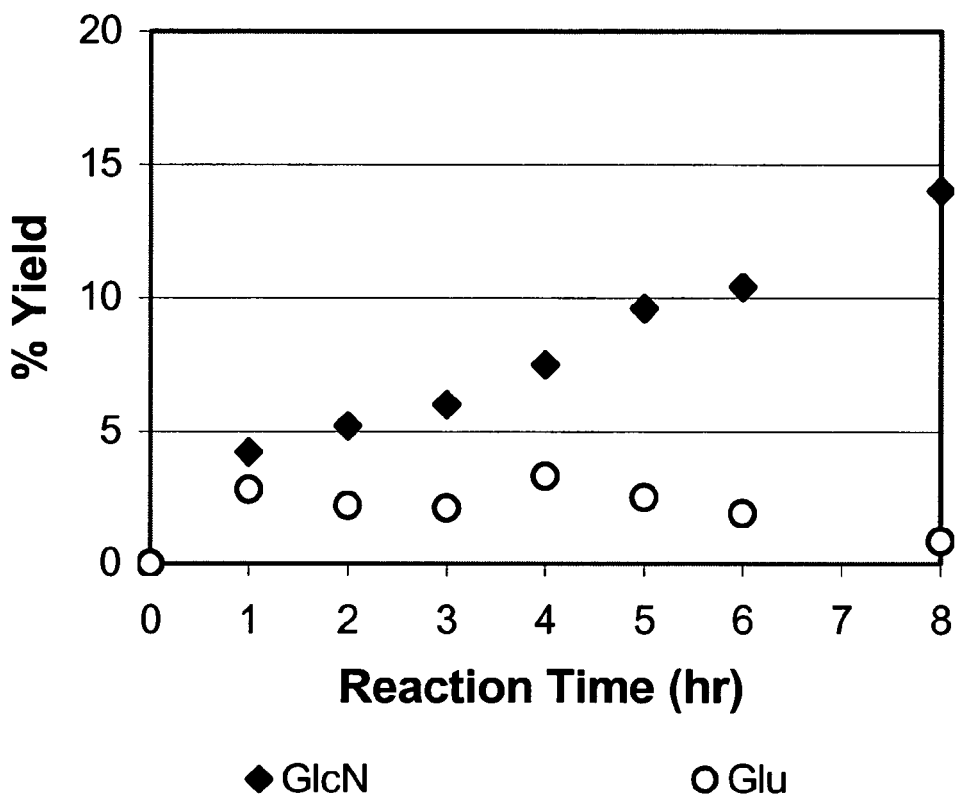
FIG. 4 is chart showing the percent yield of glucosamine in an embodiment of the disclosed glucosamine composition produced using an embodiment of the glucosamine composition methods.
Figure 5:
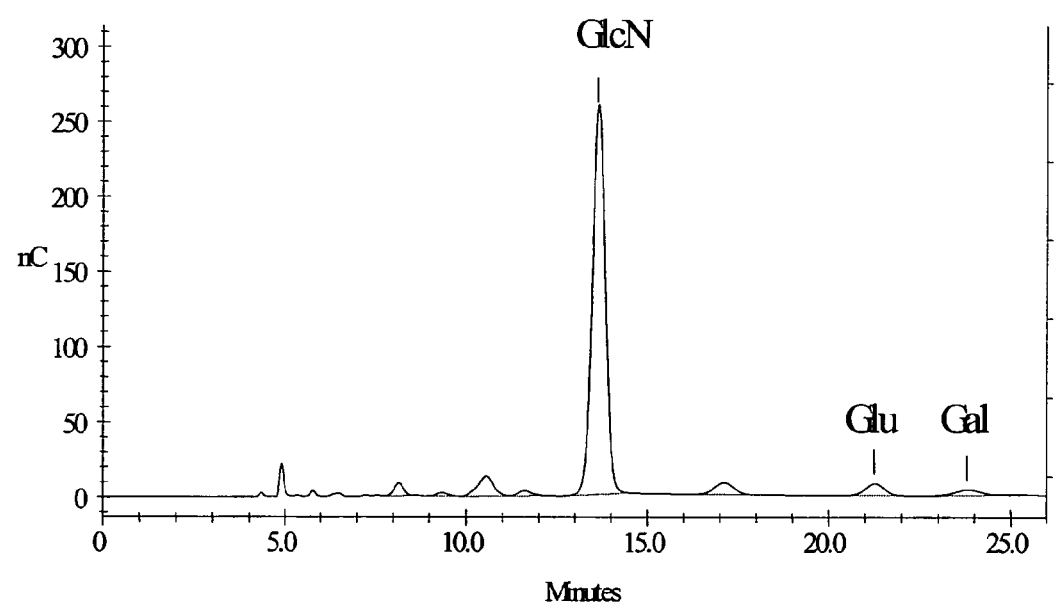
FIG. 5 is a chromatogram of an embodiment of the disclosed glucosamine compositions.

The results are provided in FIG. 4, which shows a chart indicating glucosamine production, and shows that the glucosamine was increasingly produced as the reaction ran through 8 hours, but that the amount of glucose diminished after 4 hours. After 8 hours the glucosamine produced in the yield of 14 percent. A chromatogram of the product is shown in FIG. 5.

Figure 6:
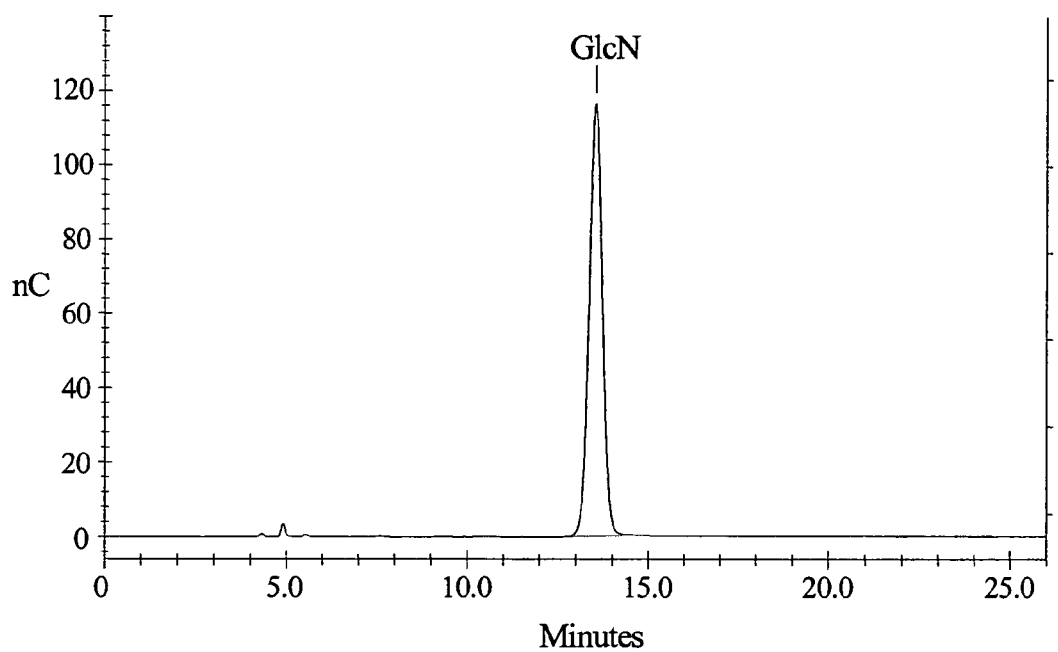
FIG. 6 is a chromatogram of an embodiment of the disclosed glucosamine compositions.

Following reaction, the mixture was filtered, and the filtrate evaporated using a rotating evaporator manufactured by RotaVap to increase the glucosamine concentration of the solution. The final volume was reduced to 10 to 20 ml. To this solution was added 20 ml of ethanol and the solution swirled to promote precipitation of glucosamine and enhance yield. These glucosamine precipitates were obtained by filtration and were further washed with alcohol until the color became white. FIG. 6 shows a chromatogram of the product, indicating greater than 97 percent glucosamine in the glucosamine composition.

Example 2

Example 1 was repeated, but the pretreated biomass was maintained under reflux conditions for 13 hours. The resulting glucosamine composition contained greater than 98 percent glucosamine.

The foregoing detailed description and examples have been given for clarity of understanding only. No unnecessary limitations are to be understood from this description or examples. The invention is not limited to the exact details shown and described, for variations will be included within the invention defined by the claims.

Example 3

Filtered biomass (3900 g) from a citric acid production process was combined with 100 mL concentrated hydrochloric acid and 4.5 L water. The resulting solution (0.5% HCl, 7.8% biomass solids) was maintained at 90-100° C. for 2 hours. The reaction mixture (71.9 g) was filtered and washed with 5 portions of water at 60-70° C. for a total of 400 mL wash. The washed biomass solids weighed 31.5 g and were found to contain 12.5% solids upon drying. The washed biomass solids therefore contained 3.9 g solids out of 71.9 g, or 5.4% solids after mild acid treatment as described above. When compared to the initial 7.8% solids prior to the mild acid treatment a 31% reduction in biomass solids was calculated.

To estimate the amount of the desirable component of the filtered biomass (chitin) sacrificed during the mild acid treatment an aggressive acid treatment was conducted using both pretreated and non-pretreated biomass to produce glucosamine hydrochloride in the following manner:

Dried (pretreated or non-pretreated) biomass (0.40 g) was combined with 3.60 g of 22.5% hydrochloric acid in a small test tube. The resulting solutions (20% HCl, 10.0% biomass solids) were held at 105° C. for 2.5 hours in a heat block. Dionex HPLC analysis of the two acid hydrolyzed samples allowed the percent glucosamine hydrochloride by weight to be determined and compared. Specifically, the amount of free glucosamine was determined using high performance anion-exchange chromatography with pulsed amperometric detection (HPAEC-PAD). The system consisted of an EG40 eluent generator, GP50 gradient pump, AS40 autosampler, LC25 column oven, and ED40 electrochemical detector, all produced by Dionex Corporation, Sunnyvale, Calif., U.S.A. The method was adapted from Dionex Corporation Technical Note 40, incorporated herein by reference. A Dionex CarboPac PA-20 column was used rather than a PA-10 column. The eluent was 8 mM KOH at 0.5 mL/min. The column and detector were maintained at 30° C. The injection volume was 10 µL. The standard was glucosamine hydrochloride at 10.8 mg/L. Samples were diluted with deionized water, ASTM Type II, and filtered through 0.2 µm vial filters in an autosampler. Multiple standards were analyzed before and after each sample set.

The non-pretreated biomass sample contained 2.1% glucosamine hydrochloride. The maximum theoretical amount of glucosamine hydrochloride attainable from the pretreated biomass is 3.0% (assumes all 31% reduction in biomass solids is non-chitin). The pretreated biomass sample was measured at 2.7% glucosamine hydrochloride by weight. Thus, mild acid pretreatment resulted in a 29% chitin-enrichment of the biomass solids, yet reduced the yield of glucosamine hydrochloride from the original biomass by 10%.

Example 4

Filtered biomass (3900 g) from a citric acid production process was combined with 100 mL concentrated hydrochloric acid and 4.5 L water. The resulting solution (0.5% HCl, 7.8% biomass solids) was held at 90-100° C. for 20 hours. The reaction mixture (95.2 g) was filtered and washed with 5 portions of water at 54-70° C. for a total of 320 mL wash. The washed biomass solids weighed 26.9 g and were found to contain 16.0% solids upon drying. The washed biomass solids therefore contained 4.3 g solids out of 95.2 g, or 4.5% solids after a mild acid treatment as described above. When compared to the initial 7.8% solids prior to the mild acid treatment one can calculate a 42% reduction in biomass solids was obtained.

To estimate the amount of the desirable component of the filtered biomass (chitin) sacrificed during the mild acid treatment, an aggressive acid treatment was conducted using both pretreated and non-pretreated biomass to produce glucosamine hydrochloride in the following manner:

Dried (pretreated or non-pretreated) biomass (0.40 g) was combined with 3.60 g of 22.5% hydrochloric acid in a small test tube. The resulting solutions (20% HCl, 10.0% biomass solids) were held at 105° C. for 2.5 hours in a heat block. Dionex HPLC analysis (performed as described in Example 4) of the two acid hydrolyzed samples allowed the percent glucosamine hydrochloride by weight to be determined and compared. The non-pretreated biomass sample contained 2.1% glucosamine hydrochloride. The maximum theoretical amount of glucosamine hydrochloride attainable from the pretreated biomass is 3.6% (assuming all 42% reduction in biomass solids is non-chitin). The pretreated biomass sample was measured at 3.0% glucosamine hydrochloride by weight. Thus, mild acid pretreatment resulted in a 43% chitin-enrichment of the biomass solids yet reduced the yield of glucosamine hydrochloride from the original biomass by 17%.

Example 5

Filtered biomass (2000 g) from a citric acid production process was combined with 3000 g of a 7.5% hydrochloric acid solution. The resulting solution (4.5% HCl, 6.0% biomass solids) was held at 90-100° C. for 2 hours. A portion (40.7 g) of the reaction mixture was transferred to a 50 mL centrifuge tube. The sample was centrifuged and the liquor was decanted. The remaining solids were subsequently washed five times with 25-30 mL portions of NaOH solution (pH 13.1) then washed four times with 25 mL portions of HCl solution (pH 1.3). A final adjustment of the pH to near neutral afforded the isolation of washed biomass solids by decantation. The biomass solids weighed 5.9 g and were found to contain 14.2% solids upon drying. The washed biomass solids therefore contained 0.84 g solids out of 40.7 g, or 2.1% solids after mild acid treatment as described above. When compared to the initial 6.0% solids prior to the mild acid treatment a 65% reduction in biomass solids was calculated.

To estimate the amount of the desirable component of the filtered biomass (chitin) sacrificed during the mild acid treatment an aggressive acid treatment was conducted using both pretreated and non-pretreated biomass to produce glucosamine hydrochloride in the following manner:

Dried (pretreated or non-pretreated) biomass (0.10 g) was combined with 1.90 g of 20.3% hydrochloric acid in a small test tube. The resulting solutions (19.3% HCl, 5.0% biomass solids) were held at 105° C. for 4 hours in a heat block. Dionex HPLC analysis (performed as described above) of the two acid hydrolyzed samples allowed the percent glucosamine hydrochloride by weight to be determined and compared. The non-pretreated biomass sample contained 1.0% glucosamine hydrochloride. The maximum theoretical amount of glucosamine hydrochloride attainable from the pretreated biomass is 2.9% (assuming all 65% reduction in biomass solids is non-chitin). The pretreated biomass sample was measured at 2.1% glucosamine hydrochloride by weight. Thus, mild acid pretreatment resulted in a 110% chitin-enrichment of the biomass solids, yet reduced the yield of glucosamine hydrochloride from the original biomass by 28%.

Example 6

Filtered biomass (3000 g) from a citric acid production process was combined with 3000 g of 8.7% sodium hydroxide solution. The resulting solution (4.4% NaOH, 8.1% biomass solids) was held at 90-100° C. for 45 minutes. The reaction mixture was filtered and washed with water at 40-50° C. until the percent NaOH remaining in the washed biomass solids was less than 0.06%. The washed biomass solids weighed 1479 g and were found to contain 22.9% solids upon drying. The washed biomass solids therefore contained 339 g solids out of 6000 g or 5.7% solids after mild base treatment as described above. When compared to the initial 8.1% solids prior to the mild base treatment a 30% reduction in biomass solids was calculated.

The washed biomass solids obtained from mild base treatment were subsequently subjected to a mild acid treatment. The washed biomass solids (1310 g) was combined with 3665 g of 5.5% hydrochloric acid solution and 25 g of glacial acetic acid. The resulting solution (4.0% HCl, 0.5% acetic acid, 6.0% biomass solids) was held at 90-100° C. for 3.5 hours. At this time a portion, 944 g, of the reaction mixture was filtered and washed with 1409 g water in two portions. The washed biomass solids weighed 298 g and were found to contain 12.5% solids upon drying. The washed biomass solids therefore contained 37.3 g solids out of 944 g, or 4.0% solids after mild acid treatment. When compared to the initial 6.0% solids of the mild acid treatment a 33% reduction in biomass solids was calculated. An overall reduction of 53% in biomass solids resulted from the combined effect of mild base treatment followed by mild acid treatment.

To estimate the amount of the desirable component of the filtered biomass (chitin) sacrificed during the mild base and mild acid treatments, an aggressive acid treatment was conducted using both pretreated and non-pretreated biomass to produce glucosamine hydrochloride in the following manner:

Dried (pretreated or non-pretreated) biomass (0.10 g) was combined with 1.90 g of 22.8% hydrochloric acid in a small test tube. The resulting solutions (21.6% HCl, 5.1% biomass solids) were held at 105° C. for 4 hours in a heat block. Dionex HPLC analysis (performed as described above) of the three acid hydrolyzed samples allowed the percent glucosamine hydrochloride by weight to be determined and compared. The non-pretreated biomass sample contained 0.92% glucosamine hydrochloride. The maximum theoretical amount of glucosamine hydrochloride attainable from the mild base pretreated biomass is 1.3% (assuming all 30% reduction in biomass solids is non-chitin). The mild base pretreated biomass sample was measured at 1.3% glucosamine hydrochloride by weight. Thus, mild base pretreatment resulted in a 41% chitin-enrichment of the biomass solids without a reduction in the yield of glucosamine hydrochloride from the original biomass. The maximum theoretical amount of glucosamine hydrochloride attainable from the mild acid pretreated biomass is 2.0% (assumes the overall 54% reduction in biomass solids is non-chitin). The mild acid pretreated biomass sample was measured at 1.5% glucosamine hydrochloride by weight. Thus, mild acid pretreatment following the mild base pretreatment resulted in a 63% chitin-enrichment of the original biomass solids, yet reduced the yield of glucosamine hydrochloride from the original biomass by 25%.

Example 7

A biomass sample from a citric acid fermentation process was combined with HCL to form a slurry of 13% HCl and 10.5% biomass solids. The slurry was placed in a sealed reactor and brought to 113° C. for 10 hours. Samples of the resulting composition were taken at one hour intervals and were analyzed for glucosamine. These results were then converted to a yield based on the theoretical amount of chitin in the biomass.

This procedure was repeated using slurries of 11% and 9% HCl, with biomass solids of 12%. The results are shown in the following table.

| % wt/wt HCl | Average Temperature, ° C. | Average Pressure, psig | Time in hours | % yield based on original biomass theoretical chitin |
|---|---|---|---|---|
| 13 | 113 | 13 | 5.3 | 79 |
| 11 | 113 | 13 | 6.8 | 75 |
| 9 | 113 | 12 | 11 | 70 |

Example 8

Citric acid fermentation biomass (*A. niger*) was mixed with hydrochloric acid (JT Baker's 37 percent Reagent Grade) and placed in a sealed small scale microwave digestion bomb, available from Alltech. Prepared samples were placed in a laboratory vacuum oven with no vacuum applied. The oven was capable of maintaining a temperature of 160° C. Samples were prepared and treated under the conditions listed in Table 3 below.

Samples were diluted with nanopure water to a concentration range of within the standard range (<10 mg/L GAP) using a Dionex HPLC system (performing the analyses as described above). Specifically, two dilutions were performed, a 1:50 dilution followed by a 1:6 dilution. The diluted samples were filtered through a 0.45 μm filter and analyzed for dextrose and glucosamine concentrations using a Dionex HPLC system.

The results are tabulated in Table 3 below. Because each trial had (at the most) four sample points, the highest glucosamine results for each trial were recorded. The sample results were not corrected for any evaporative losses in the sample during the reaction.

TABLE 3

| Acid Conc (wt. %) | Biomass Conc (wt. %) | Time (hours) | Temperature (° C.) | % yield based on original biomass theoretical chitin |
|---|---|---|---|---|
| 2.2 | 3.9 | 4 | 160 | 18.2 |
| 2.2 | 3.9 | 4 | 160 | 10.2 |
| 2.2 | 3.9 | 2.5 | 160 | 12.6 |
| 2.2 | 3.9 | 7 | 140 | 11.6 |
| 6.2 | 5.2 | 5.5 | 140 | 17.0 |
| 6.2 | 10.1 | 5.5 | 140 | 17.9 |
| 5.7 | 5.8 | 6 | 160 | 16.3 |
| 6.2 | 10.0 | 4 | 140 | 18.4 |

*Percent yields based on 24% theoretical chitin in dry biomass Glucosamine yields are not adjusted for evaporative losses. The evaporative loss is shown to provide an indication of a source of error in the bench top test.

The results of these embodiments of the glucosamine compositions as shown in Examples 8 and 9 indicate that using the disclosed increased temperature and or pressure methods for making the same indicate that significantly lower amounts or concentrations of hydrochloric acid are required to produce significant yields of the glucosamine compositions.

For all sample points selected for Table 3 the dextrose concentrations were close to zero.

Example 9

A variety of embodiments of food supplements incorporating particular embodiments of the glucosamine composition is shown in Table 4 below. The food supplements in these particular examples are in tablet, capsule, chewable, liquid, or food bar, form but could be in any suitable food supplement physical form.

TABLE 4

| | % |
|---|---|
| Tablet Composition Components | |
| Glucosamine HCL | 57 |
| Binder | 40 |
| Dispersant | 2 |
| Flow Enhancer | 0.7 |
| Lubricant | 0.3 |
| Juice-Based Beverage Composition Components | |
| Water | 92.93 |
| 43 High Fructose Corn Syrup | 6.0 |
| 25% Citric Acid | 0.5 |
| Fruit Punch Flavor | 0.1 |
| Glucosamine HCL | 0.312 |
| Sodium Chloride | 0.05 |
| Carboxymethyl Cellulose | 0.05 |
| 10% Red 40 | 0.035 |
| Monopotassium Phosphate | 0.025 |
| Potassium Benzoate | 0.00021 |
| Chew Composition Components | |
| 43 High Maltose Corn Syrup | 23.17 |
| 42 High Fructose Corn Syrup | 18.75 |
| Sucrose | 10.19 |
| Glucosamine HCL | 16.68 |
| Evaporated Milk | 7.39 |
| Water | 7.39 |

TABLE 4-continued

| | % |
|---|---|
| Coconut oil, 92° F. Melting Point | 6.49 |
| Lecithin | 0.14 |
| Glycerol Monostearate | 0.14 |
| Salt | 0.3 |
| Chocolate-coating for bar | 9.29 |
| Flavor | 0.1 |
| Nutrition Bar Composition Components | |
| High Fructose Corn Syrup | 20 |
| Dark Chocolate Confectionery Wafers | 20 |
| Soy Protein Isolate | 15 |
| High Maltose Corn Syrup | 10 |
| Honey | 6 |
| Whey Protein Concentrate | 7 |
| Gerkens 10/12 Russet Plus Cocoa | 5 |
| Maltodextrin | 4 |
| Water | 3 |
| Canola Oil | 4 |
| Unsweetened Chocolate | 2 |
| Glycerine | 2 |
| Fine Flake Salt | 1 |
| Glucosamine HCL | 1 |

SUMMARY

A number of reactions were done to examine increasing the temperature and/or pressure of the reaction for the production of glucosamine compositions from fermentation mycelia while, in certain examples, decreasing the reaction time. Using the disclosed methods for the glucosamine composition production, it was shown that the reaction is feasible at up to at least 160° C. with a hydrochloric acid concentration as low as 2% and a reaction time of two to four hours. About 50% percent less HCl was needed to produce these results as compared to the methods where neither the reaction temperature nor the pressure was increased. The biomass concentration in the reaction is approximately up to 20 percent biomass on a dry basis. The expected yield of glucosamine from fermentation mycelia is 15 to 19 percent based on the starting dry weight of mycelia. This is in the same range or only slightly below that of the aggressive acid method and/or the mild/aggressive acid methods set forth above.

While the methods and glucosamine compositions disclosed herein may be modified, specifics thereof have been shown by way of example and are described in detail. It should be understood, however, that the specific embodiments disclosed and described are not to be interpreted as limiting the claimed invention.

We claim:

1. A method of making a glucosamine composition comprising:
    (a) providing a source of chitin-containing fungal biomass having cells with cell walls having proteins, lipids and/or polysaccharides therein;
    (b) pretreating the chitin-containing fungal biomass with a first acidic solution comprising HCl at a concentration of from about 0.05 to about 20% to break down the cell walls of the fungal biomass and release proteins, lipids and/or polysaccharides therein, without converting a significant amount of chitin to glucosamine; and
    (c) converting the chitin in remaining solid fungal biomass to glucosamine to form the glucosamine composition using a second acidic solution comprising HCl.

2. The method of claim 1 wherein solid fungal biomass is separated from the proteins, lipids and/or polysaccharides after the pretreating and prior to converting the chitin in the remaining solid fungal biomass to glucosamine.

3. The method of claim 1 wherein the first acidic solution comprises hydrochloric acid at a concentration of from about 0.5 to 12%.

4. The method of claim 1 wherein the breaking down the cell walls of the fungal biomass comprises treating the fungal biomass at a temperature of from about 60° C. to about reflux temperature of a mixture of the fungal biomass and first acidic solution.

5. The method of claim 1 wherein the converting the chitin to glucosamine comprises reacting the chitin with a second acidic solution having a concentration of from about 5 to about 20%.

6. The method of claim 1 wherein the converting the chitin to glucosamine comprises reacting the chitin with the HCl having a concentration of from about 1 to about 2%.

7. The method of claim 1 wherein the first acidic solution has an acid concentration of less than about 20% and wherein the fungal biomass and first acidic solution are mixed at a reaction temperature of less than about 100° C. for a reaction period of less than about 4 hours.

8. The method of claim 1 wherein the fungal biomass is treated with an alkaline solution prior to breaking down of the cell walls with the first acidic solution.

9. The method of claim 1 wherein the fungal biomass is treated mechanically to break down the cell walls prior to the pretreatment with the first acidic solution.

10. The method of claim 1, wherein the converting step comprises utilizing HCl having a concentration of less than about 20%.

11. The method of claim 1, wherein the converting step comprises reacting the chitin in the remaining solid fungal biomass with the second acidic solution comprising HCl at a temperature of at or about a reflux temperature of the remaining solid fungal biomass and second acidic solution mixture.

12. The method of claim 1, wherein the first acidic solution has an acid concentration of less than about 5%.

13. The method of claim 1, further comprising mixing the glucosamine composition with a dispersant and/or a binder to form a food supplement.

14. A method of obtaining glucosamine from fungal biomass, the method comprising the steps of:
  (a) providing a fungal biomass;
  (b) pretreating the fungal biomass with an alkaline solution to break down cell walls of the fungal biomass and release proteins, lipids and/or polysaccharides therein, without converting a significant amount of chitin to glucosamine;
  (c) reacting the fungal biomass in hydrochloric acid with an acid concentration and at a reaction temperature and for a reaction period sufficient to convert chitin in the fungal biomass to glucosamine;
  (d) separating the glucosamine from the acidic solution; and
  (e) forming the glucosamine into a food supplement.

15. The method of claim 14 wherein the hydrochloric acid has a concentration of from about 5 to about 20%.

16. The method of claim 14 wherein the reaction temperature is greater than about 80° C. and is reacted for a period of at least 4 hours.

17. The method of claim 14 wherein the alkaline solution comprises sodium hydroxide at a concentration of from about 1 to about 4%.

18. The method of claim 14, further comprising forming the glucosamine into a food supplement composition.

19. A method of obtaining glucosamine from fungal biomass, the method comprising the steps of:
  (a) providing a chitin-containinq fungal biomass;
  (b) reacting the fungal biomass in an acidic solution comprising HCl with an acid concentration of 9% to 20% and at a reaction temperature of from about 90° C. to about 160° C. and for a period sufficient for said reaction to convert at least about 50% of the chitin in the fungal biomass to qlucosamine wherein the reacting of fungal biomass in an acidic solution is performed in a sealed container that allows pressure therein to increase as a result of the reaction;
  (c) separating the glucosamine from the acidic solution; and
  (d) wherein the reaction temperature is from about 105° C. or greater and the reaction takes place at a pressure of about 2 atmospheres or greater.

20. A method of making a glucosamine composition comprising:
  (a) providing a source of chitin-containing fungal biomass having cell walls containing proteins, lipids and/or polysaccharides therein;
  (b) pretreating the biomass with an acidic solution comprising HCl at a temperature of from about 60° C. to about reflux temperature of a mixture of the acidic solution and biomass to release the proteins, lipids and/or polysaccharides without converting a significant amount of chitin to glucosamine;
  (c) converting the chitin in the fungal biomass to glucosamine after the pretreatment step; and
  (d) wherein a commercial-scale amount of the glucosamine composition is produced.

21. A method of making a glucosamine composition comprising:
  (a) providing a source of chitin-containing fungal biomass having cell walls containing proteins, lipids and/or polysaccharides therein;
  (b) pretreating the fungal biomass breaking down the cell walls of the fungal biomass and releasing the proteins, lipids and/or polysaccharides in liquid form without converting a significant amount of chitin to glucosamine utilizing one or more of the following pretreatments,
    (i) pretreating the chitin-containing fungal biomass with a first acidic solution comprising HCl at a concentration of from about 0.05 to about 20% acid;
    (ii) pretreating the chitin-containing fungal biomass with an alkaline solution prior to breaking down of the cell walls with the first acidic solution;
    (iii) pretreating the fungal biomass mechanically to break down the cell walls prior to the pretreatment with the first acidic solution;
  (c) separating solids from the proteins, lipids and/or polysaccharides in liquid form; and
  (d) treating the separated solids with HCl to convert chitin therein to glucosamine and separating the glucosamine in a manner such that it is suitable for use in a food supplement.

22. A method of making a glucosamine composition comprising:
  (a) providing a source of chitin-containing fungal biomass having cells with cell walls and containing proteins, lipids and/or polysaccharides in the cells;
  (b) pretreating the fungal biomass breaking down the cell walls of the fungal biomass and releasing the proteins, lipids and/or polysaccharides in liquid form without converting a significant amount of chitin to glucosamine utilizing one or more of the following pretreatments,
    (i) pretreating the chitin-containing fungal biomass with a first acidic solution comprising HCl at a concentration of from about 0.05 to about 20% acid;

(ii) pretreating the chitin-containing fungal biomass with an alkaline solution prior to breaking down of the cell walls with the first acidic solution;
(iii) pretreating the fungal biomass mechanically to break down the cell walls;
(c) separating solids from the proteins, lipids and/or polysaccharides in liquid form;
(d) treating the separated solids with HCl to convert chitin therein to glucosamine;
(e) separating the glucosamine from the HCl; and
(f) forming the glucosamine into a food supplement composition.

* * * * *